(12) United States Patent
Gao et al.

(10) Patent No.: US 11,647,978 B2
(45) Date of Patent: May 16, 2023

(54) PULMONARY ARTERY PRESSURE CHANGE MONITOR

(71) Applicants: Cardiac Motion, LLC, Truckee, CA (US); The Regents of The University of California, Oakland, CA (US)

(72) Inventors: Xiaomeng Gao, Dublin, CA (US); Xiaonan Jiang, Davis, CA (US); Xiaoguang Liu, Davis, CA (US); Dennis Matthews, Meadow Vista, CA (US); Saul Schaefer, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 17/102,838

(22) Filed: Nov. 24, 2020

(65) Prior Publication Data
US 2021/0212657 A1 Jul. 15, 2021

Related U.S. Application Data

(60) Provisional application No. 63/035,394, filed on Jun. 5, 2020, provisional application No. 62/940,025, filed on Nov. 25, 2019.

(51) Int. Cl.
*A61B 8/04* (2006.01)
*A61B 8/02* (2006.01)
*A61B 8/08* (2006.01)

(52) U.S. Cl.
CPC .............. *A61B 8/04* (2013.01); *A61B 8/02* (2013.01); *A61B 8/08* (2013.01); *A61B 8/488* (2013.01); *A61B 8/5207* (2013.01)

(58) Field of Classification Search
CPC .. A61B 8/08; A61B 8/488; A61B 8/02; A61B 8/04; A61B 8/5207
See application file for complete search history.

(56) References Cited

U.S. PATENT DOCUMENTS

| 4,881,549 A | 11/1989 | Rhyne |
| 5,274,271 A | 12/1993 | McEwan |

(Continued)

FOREIGN PATENT DOCUMENTS

| CN | 202669497 U | 1/2013 |
| EP | 2368492 A1 | 9/2011 |

(Continued)

OTHER PUBLICATIONS

Wharton et al.; Changes in left ventricular wall movement after acute myocardial infarction measured by reflected ultrasound. published on Oct. 9, 1971; Br Med J. Oct. 9, 1971;4(5779):75-7. (Year: 1971).*

(Continued)

*Primary Examiner* — Chao Sheng

(57) ABSTRACT

The present disclosure describes systems, methods, and devices to infer changes in pulmonary artery pressure in a subject using Doppler radar. A portable, non-invasive device for non-invasively measuring right ventricular cardiac motion that can be used in a subject's home can infer pulmonary artery pressure changes to increase patient compliance and mitigate the likelihood of heart decompensation. A mobile pulmonary artery pressure monitor can be especially useful to patients with congestive heart failure who are elderly, incapacitated, or do not have easy access to a clinic, doctor's office, or hospital.

22 Claims, 27 Drawing Sheets

(56) References Cited

U.S. PATENT DOCUMENTS

| | | | |
|---|---|---|---|
| 5,292,348 | A | 3/1994 | Saumarez et al. |
| 5,511,553 | A | 4/1996 | Segalowitz |
| 5,573,012 | A | 11/1996 | McEwan |
| 5,738,102 | A | 4/1998 | Lemelson |
| 5,766,208 | A | 6/1998 | McEwan |
| 6,681,404 | B1 | 1/2004 | Adlard et al. |
| 8,068,051 | B1 | 11/2011 | Osterweil |
| 8,378,879 | B2 | 2/2013 | Lewis et al. |
| 8,463,361 | B2 | 6/2013 | Tupin et al. |
| 8,494,615 | B2 | 7/2013 | Melamed et al. |
| 8,502,729 | B2 | 8/2013 | Leach, Jr. et al. |
| 8,562,526 | B2 | 10/2013 | Heneghan et al. |
| 2004/0015087 | A1 | 1/2004 | Boric-Lubecke et al. |
| 2004/0106954 | A1 | 6/2004 | Whitehurst et al. |
| 2005/0052322 | A1 | 3/2005 | Park et al. |
| 2005/0073424 | A1 | 4/2005 | Ruoss et al. |
| 2005/0100376 | A1 | 5/2005 | Omotani |
| 2006/0094937 | A1 | 5/2006 | Immoreev et al. |
| 2008/0074307 | A1 | 3/2008 | Boric-Lubecke et al. |
| 2008/0294019 | A1 | 11/2008 | Tran |
| 2008/0319498 | A1* | 12/2008 | Hedberg ............ A61B 5/686 607/17 |
| 2009/0048500 | A1 | 2/2009 | Corn |
| 2009/0203972 | A1 | 8/2009 | Heneghan et al. |
| 2009/0227882 | A1 | 9/2009 | Foo |
| 2009/0278728 | A1 | 11/2009 | Morgan et al. |
| 2010/0056907 | A1* | 3/2010 | Rappaport ............ A61B 5/05 600/595 |
| 2010/0113945 | A1 | 5/2010 | Ryan |
| 2010/0152600 | A1 | 6/2010 | Droitcour et al. |
| 2010/0179438 | A1 | 7/2010 | Heneghan et al. |
| 2010/0245091 | A1 | 9/2010 | Singh et al. |
| 2011/0218586 | A1 | 9/2011 | Li |
| 2013/0053653 | A1 | 2/2013 | Cuddihy et al. |
| 2013/0135137 | A1 | 5/2013 | Mulder et al. |
| 2013/0281800 | A1 | 10/2013 | Saroka et al. |
| 2015/0359463 | A1* | 12/2015 | Matthews ............ A61B 5/024 600/407 |

FOREIGN PATENT DOCUMENTS

| | | | | |
|---|---|---|---|---|
| WO | WO-2004109316 | A2 | 12/2004 | |
| WO | WO-2007101343 | A1 | 9/2007 | |
| WO | WO-2007124126 | A2 | 11/2007 | |
| WO | WO-2007143535 | A2 | 12/2007 | |
| WO | WO-2008026157 | A2 | 3/2008 | |
| WO | WO-2008057883 | A2 | 5/2008 | |
| WO | WO-2008148040 | A1 | 12/2008 | |
| WO | WO-2009031149 | A2 * | 3/2009 | ............ A61B 5/00 |
| WO | WO-2007052108 | A3 | 4/2009 | |
| WO | WO-2011146517 | A2 | 11/2011 | |
| WO | WO-2012148280 | A1 | 11/2012 | |
| WO | WO-2013118121 | A1 | 8/2013 | |
| WO | WO-2018144968 | A1 | 8/2018 | |
| WO | WO-2021108357 | A1 | 6/2021 | |

OTHER PUBLICATIONS

Nagueh et al.; Echocardiographic Evaluation of Hemodynamics in Patients With Decompensated Systolic Heart Failure; published on Mar. 11, 2011; Circulation: Cardiovascular Imaging. 2011;4:220-227 (Year: 2011).*

Novo Matos et al.; Transient Myocardial Thickening in Cats Associated with Heart Failure; published on Dec. 15, 2017; J Vet Intern Med. Jan. 2018;32(1):48-56 (Year: 2017).*

Robbins et al.; Prevalence and severity of mitral regurgitation in chronic systolic heart failure; published on Feb. 1, 2003; Am J Cardiol. Feb. 1, 2003;91(3):360-2 (Year: 2003).*

Tidholm et al.; Tissue Doppler and Strain Imaging in Dogs with Myxomatous Mitral Valve Disease in Different Stages of Congestive Heart Failure; published on Oct. 27, 2009; J Vet Intern Med. Nov.-Dec. 2009;23(6):1197-207. (Year: 2009).*

Heart failure—Symptoms and causes—Mayo Clinic; https://www.mayoclinic.org/diseases-conditions/heart-failure/symptoms-causes/syc-20373142 (Year: 2021).*

Haddad et al.; Right Ventricular Function in Cardiovascular Disease, Part I Anatomy, Physiology, Aging, and Functional Assessment of the Right Ventricle; published on Mar. 18, 2008; Circulation; vol. 117, Issue 11, pp. 1436-1448 (Year: 2008).*

Cheung, Yiu-fai; The role of 3D wall motion tracking in heart failure; published on Sep. 4, 2012; Nature Reviews Cardiology, vol. 9, pp. 644-657 (2012) (Year: 2012).*

Azevedo, et al. Micropower impulse radar. Science and Technology Review. Jan./Feb. 1996; 16-29.

Brovoll, et al., Optimal frequency range for medical radar measurements of human Heartbeats using body-contact radar. 2013 35th Annual International Conference of the IEEE Engineering in Medicine and Biology Society (EMBC), Osaka, 2013, pp. 1752-1755.

International search report and written opinion dated Mar. 25, 2021 for PCT Application No. US2020/061931.

Fletcher, et al. Wearable Doppler Radar with Integrated Antenna for Patient Vital Sign Monitoring, RSW (2010) pp. 276-279.

International search report and written opinion dated Nov. 4, 2015 for PCT Application No. US2015/035405.

Oyvind et al. Detecting changes in the human heartbeat with on-body radar. Radar Conference (RADAR), 2013 IEEE. DOI: 10.1109/RADAR.2013.6586027.

Zito et al., Feasibility Study and Design of a Wearable System-on-a-Chip Pulse Radar for Contactless Cardiopulmonary Monitoring International Journal of Telemedicine and Applications, vol. 2008, Article ID 328597, 10 pages.

Guazzi et al., Pulmonary Hypertension in Heart Failure: Pathophysiology, Pathobiology, and Emerging Clinical Perspectives, Journal of the American College of Cardiology, vol. 69, Issue 13, 2017, pp. 1718-1734.

Mazimba et al., Pulmonary Artery Proportional Pulse Pressure (PAPP) Index Identifies Patients With Improved Survival From the Cardio MEMS Implantable Pulmonary Artery Pressure Monitor. Heart Lung Circ. Sep. 2021;30(9):1389-1396. doi: 10.1016/j.hlc.2021.03.004. Epub Jun. 11, 2021. PMID: 33863665.

Simon et al., Phenotyping the right ventricle in patients with pulmonary hypertension. Clin Transl Sci. Aug. 2009;2(4):294-9. doi: 10.1111/j.1752-8062.2009.00134.x. PMID: 20443908; PMCID: PMC2907237.

International search report and written opinion dated Mar. 25, 2021 for PCT Application No. PCT/US2020/061931.

* cited by examiner

| Cable | Signal |
|---|---|
| A | RA (Right Arm) |
| B | LA (Left Arm) |
| C | RL (Right Leg) |

PULMONARY ARTERY PRESSURE CHANGE MONITOR

CROSS-REFERENCE

The application claims priority to U.S. Provisional Application No. 63/035,394, filed Jun. 5, 2020, and U.S. Provisional Application No. 62/940,025, filed Nov. 25, 2019, each of which is incorporated herein by reference in its entirety.

STATEMENT REGARDING FEDERALLY SPONSORED RESEARCH OR DEVELOPMENT

The invention was made with the support of the United States government under the Small Business Technology Transfer Award #1660253 by the National Science Foundation. The government may have certain rights in the invention.

BACKGROUND

Monitoring devices that can be used in the home by heart failure patients has the potential to reduce healthcare costs by minimizing decompensation leading to rehospitalizations, to increase medication compliance, and to improve quality of life. The elderly, incapacitated, and those without easy access to healthcare facilities can greatly benefit from such home testing devices. However, current portable systems for monitoring pulmonary artery (PA) pressure are invasive and expensive, and carry the risk of significant medical complications for patients suffering from heart failure.

SUMMARY

In some embodiments, the invention provides a method of detecting a heart failure condition in a subject, comprising: a) transmitting by a transmitter a wave of energy to a heart of the subject; b) detecting by a receiver a signal reflected off the heart of the subject in response to the wave of energy transmitted to the heart of the subject, wherein the signal reflected off the heart of the subject corresponds to a motion of the heart; and c) determining based on the signal reflected off the heart of the subject whether the subject has the heart failure condition.

In some embodiments, the invention provides a method of determining a clinically-significant change in pulmonary artery pressure in a subject, comprising: a) transmitting by a transmitter a wave of energy to a heart of the subject; b) detecting by a receiver a signal reflected off the heart of the subject in response to the wave of energy transmitted to the heart of the subject, wherein the signal reflected off the heart of the subject corresponds to a motion of the heart; and c) determining based on the signal reflected off the heart of subject the clinically-significant change in pulmonary artery pressure.

In some embodiments, the invention provides a method of detecting a heart failure condition in a subject, comprising: a) during a first time period of detection: i) transmitting by a transmitter a first wave of energy to a heart of the subject; ii) detecting by a receiver a first signal reflected off the heart of the subject in response to the first wave of energy transmitted to the heart of the subject, wherein the first signal reflected off the heart of the subject corresponds to a first motion of the heart; and iii) determining a first average magnitude of the first motion of the heart over the first time period of detection; b) during a second time period of detection: i) transmitting by the transmitter a second wave of energy to the heart of the subject; ii) detecting by the receiver a second signal reflected off the heart of the subject in response to the second wave of energy transmitted to the heart of the subject, wherein the second signal reflected off the heart of the subject corresponds to a second motion of the heart; and iii) determining a second average magnitude of the second motion of the heart over the second time period of detection; c) determining a change between the first average magnitude of the first motion of the heart over the first time period of detection and the second average magnitude of the second motion of the heart over the second time period of detection; and d) determining based on the change between the first average magnitude of the first motion of the heart over the first time period of detection and the second average magnitude of the second motion of the heart over the second time period of detection whether the subject has the heart failure condition.

In some embodiments, the invention provides a method of detecting a heart failure condition in a subject, comprising: a) obtaining a first average magnitude of the first motion of the heart over a first time period of detection; b) obtaining a second average magnitude of the second motion of the heart over a second time period of detection; c) determining a change between the first average magnitude of the first motion of the heart over the first time period of detection and the second average magnitude of the second motion of the heart over the second time period of detection; and d) determining based on the change between the first average magnitude of the first motion of the heart over the first time period of detection and the second average magnitude of the second motion of the heart over the second time period of detection whether the subject has the heart failure condition.

INCORPORATION BY REFERENCE

Each patent, publication, and non-patent literature cited in the application is hereby incorporated by reference in its entirety as if each was incorporated by reference individually.

DETAILED DESCRIPTION

Figure 1:
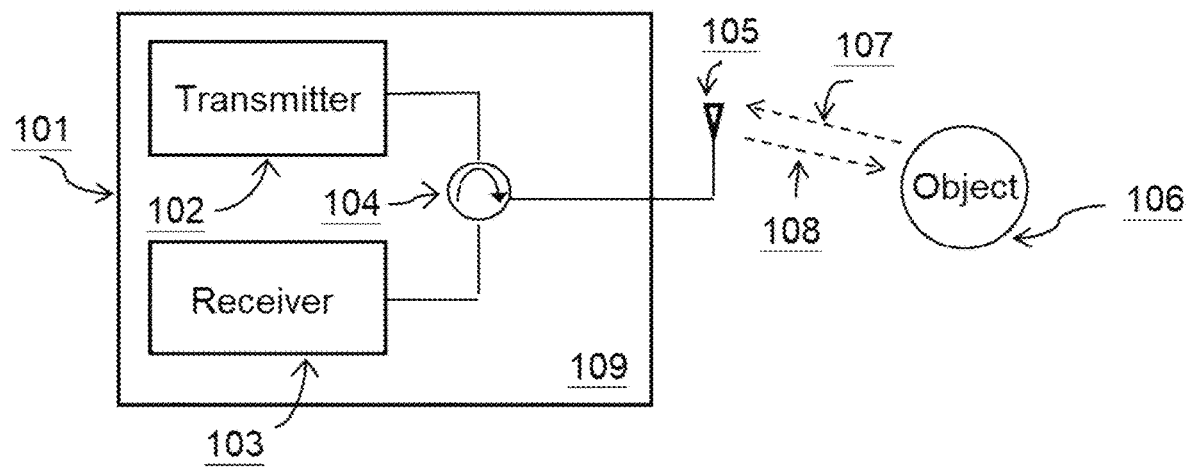
FIG. 1 depicts a representative system of the invention.

Portable cardiac monitoring devices have the potential to reduce healthcare costs and streamline the delivery of healthcare to patients who do not have immediate or easy access to healthcare facilities. A portable heart motion monitor can rapidly and conveniently infer changes in PA pressure and determine the cardiac status of patients with congestive heart failure without requiring travel to a clinic or hospital. This convenience can reduce costs by reducing frequency of hospital visits and improving outcomes due to increased patient compliance. A compact and portable heart motion monitor provides a special benefit to patients who are elderly, incapacitated, or living in remote areas, who would otherwise have to travel tediously to receive adequate healthcare. The invention described herein provides simple, cost-effective, and efficient systems to infer PA pressure changes that could signal heart failure decompensation from anywhere that the patient goes, especially in the comfort of the patient's home. Such information enables clinical care specialists to modify medical interventions to medically treat heart failure in the early stages of decompensation.

After initial diagnosis or hospitalization of heart failure patients, re-admission occurs for 20-25% of patients, with 65,000 patients re-admitted within 30 days of discharge. These re-admissions can be prevented by appropriate outpatient monitoring and management but are often ineffective, largely due to inadequate monitoring methods and poor patient compliance. Outpatient management of heart failure requires a multi-pronged approach, including guideline-directed medication management and appropriate use of diuretics to regulate intra-vascular and total body fluid volumes. Most re-admitted patients with a heart failure exacerbation (decompensation) experience fluid overload, as evidenced by weight gain, shortness of breath, pulmonary rhonchi edema, and lower extremity edema. With invasive monitoring, these patients have increased central venous pressure, increased PA pressure, and impaired ventricular function.

Patients at risk for decompensation can be monitored for signs of volume overload (direct or indirect) that occur early in the process of decompensation, such as elevated PA pressure. Early detection of heart decompensation can allow early implementation of interventions, such as adjusting patient medications to improve recovery rates and avoid costly hospitalization. Other diagnostic tests, such as monitoring patient weight, blood pressure, and heart rate, provide relatively crude information that often change late in the course of disease.

A standard diagnostic test for detecting heart failure is X-ray imaging of the chest. A chest X-ray can image the lungs and heart to detect abnormalities indicative of heart malfunction. For example, a chest X-ray can show enlargement of the RV of the heart and/or the pulmonary arteries that is characteristic of pulmonary hypertension or heart failure. X-ray imaging can also reveal pulmonary vascular pathology by illustrating vessel displacement and vascularization of the lungs. However, X-ray imaging can be impractical and unsafe for at-home use without professional supervision and clinical expertise. X-ray imaging also has low sensitivity and low accuracy for mild to moderate cases, and thus, is not useful for early diagnosis of heart failure.

Another standard diagnostic test for detecting heart failure is echocardiography. Echocardiography, or a heart ultrasound, is a non-invasive imaging technique that uses sound waves to produce live images of the heart. However, echocardiography requires a significant amount of clinical expertise and cannot provide continuous monitoring. Images obtained by echocardiography can also be distorted by patient positioning.

A standard diagnostic test for detecting cardiac activity is electrocardiography. An electrocardiogram (ECG or EKG) is a recording of the electrical activity of the heart, the output of which is a series of waveforms corresponding to the electrical impulses generated by the polarization and depolarization of cardiac tissue. Although an ECG is a powerful method to glean a variety of information about a patient's cardiac status, the test requires a significant amount of clinical expertise and a visit to the clinic or hospital to obtain a clinically relevant diagnosis of cardiac disorders. This inconvenience makes the process of obtaining an ECG unappealing, especially if the subject is elderly, incapacitated, or resides in a rural area where access to a clinic can be difficult. In addition, ECG cannot directly measure mechanical movements of the heart, such as contraction and expansion of portions of the heart.

PAH is a heart failure syndrome affecting the right side of the heart. The RV of the heart pumps blood to the pulmonary circulation and can respond to changes in PA pressure. In early-stage PAH, for example, the RV tends to remain well-preserved with little or no increase in volume. This symptom is also observed in cases of pulmonary embolism in which the PA pressure increases due to an obstruction in the pulmonary vasculature. For this reason, RV size and function can be used as metrics for determining course of therapy for cases of pulmonary embolism. As PAH progresses, patients have enlarged RVs with reduced function. Thus, motions of the RV can directly reflect changes in PA pressure and the progression of PAH. Detecting RV size and function can provide a mechanism to non-invasive monitoring of PA pressure changes in patients at risk of heart failure.

Doppler radar sensing provides a sensitive, non-invasive method of measuring expansion and contraction of a portion of the heart. For example, Doppler radar can be used for measuring expansion and contraction of the RV. Thus, Doppler radar sensing provides a non-invasive method of monitoring elevated PA pressure changes in patients with heart failure due to decompensation. In combination with other methods of measuring thoracic fluid status and vital signs, Doppler radar serves as a surrogate or reflection of PA pressure. Doppler radar non-invasive sensing of the heart can contribute to the assessment of decompensation for heart failure patients and patients at risk for heart failure.

Described herein are systems, methods, and devices for detecting a heart failure condition in a subject by: a) transmitting by a transmitter a wave of energy to a heart of the subject; b) detecting by a receiver a signal reflected off the heart of the subject in response to the wave of energy transmitted to the heart of the subject, wherein the signal reflected off the heart of the subject corresponds to a motion of the heart; and c) determining based on the signal reflected off the heart of the subject whether the subject has the heart failure condition.

Further described herein are systems, methods, and devices for detecting a heart failure condition in a subject by: a) during a first time period of detection: i) transmitting by a transmitter a first wave of energy to a heart of the subject; ii) detecting by a receiver a first signal reflected off the heart of the subject in response to the first wave of energy transmitted to the heart of the subject, wherein the first signal reflected off the heart of the subject corresponds to a first motion of the heart; and iii) determining a first average magnitude of the first motion of the heart over the first time period of detection; b) during a second time period of detection: i) transmitting by the transmitter a second wave of energy to the heart of the subject; ii) detecting by the receiver a second signal reflected off the heart of the subject in response to the second wave of energy transmitted to the heart of the subject, wherein the second signal reflected off the heart of the subject corresponds to a second motion of the heart; and iii) determining a second average magnitude of the second motion of the heart over the second time period of detection; c) determining a change between the first average magnitude of the first motion of the heart over the first time period of detection and the second average magnitude of the second motion of the heart over the second time period of detection; and d) determining based on the change between the first average magnitude of the first motion of the heart over the first time period of detection and the second average magnitude of the second motion of the heart over the second time period of detection whether the subject has the heart failure condition.

Further described herein are systems, methods, and devices for detecting a heart failure condition in a subject by: a) obtaining a first average magnitude of the first motion of the heart over a first time period of detection; b) obtaining a second average magnitude of the second motion of the heart over a second time period of detection; c) determining a change between the first average magnitude of the first motion of the heart over the first time period of detection and the second average magnitude of the second motion of the heart over the second time period of detection; and d) determining based on the change between the first average magnitude of the first motion of the heart over the first time period of detection and the second average magnitude of the second motion of the heart over the second time period of detection whether the subject has the heart failure condition.

In some embodiments, a method includes determining based on the signal reflected off the heart of the subject an average magnitude of the motion of the heart over a time period of detection. The average magnitude of the motion of the heart can increase or decrease between two time periods of detection.

Heart decompensation is characterized by the deterioration of pumped blood volume as a result of the inability of the heart to maintain blood flow. Heart failure patients can decompensate after initial successful treatment forcing them to return to in-patient hospital care. This decompensation can be diagnosed based on a measurement of pulmonary artery pulsatile pressure (PAPP), which describes pulmonary artery pressure over time. An increase in PA pressure often occurs when a patient with heart failure decompensates and develops pulmonary hypertension. This increase in PA pressure can result in decreased right ventricular function. Thus, a clinically-significant change in pulmonary artery pressure (PAP) can be determined by detection of a change in the movement capacity of the heart. The change in movement capacity can be assessed from a signal reflected from the surface of a portion of the heart. In particular, detecting an average magnitude of the motion of the surface of the right ventricle can be used to determine a clinically-significant change in PAP.

Described herein are systems, methods, and devices for determining whether a subject has a heart failure condition based on a clinically-significant change in the pulmonary artery pressure. In some embodiments, a clinically-significant change can be characterized as a change that indicates a clinical condition, for example, a heart failure condition, in a subject. The change in the pulmonary artery pressure can be based on a change in an average magnitude of a heart motion in the subject over a time period of detection. The change in an average magnitude of a heart motion can be determined based on a received signal reflected off of a surface of a portion of the heart. The clinically-significant change in pulmonary artery pressure can be an increase or a decrease.

A time period of detection of an average magnitude of motion of the heart can be a single heartbeat (cardiac cycle) of a subject, for example, at the beginning of the systole of one heartbeat and at the beginning of the diastole of the following heartbeat. During the systole, the heart muscle contracts to force blood out the heart chambers and into the vasculature. Following the systole is the diastole in which the heart muscle relaxes and allows blood to re-enter the heart from the vasculature. Systolic dysfunction occurs when the heart has reduced capability to contract, and thus, ejects less blood into the vasculature, for example, in heart failure. Diastolic dysfunction occurs when the heart has reduced capability to relax or expand, and thus, allows less blood to re-enter the heart chambers. In some embodiments, the time period of detection of an average magnitude of motion of the heart is multiple heartbeats of a subject.

A time period of detection can be about 1 second to about 20 seconds, about 1 second to about 30 seconds, or about 1 second to about 60 seconds. In some embodiments, a time period of detection is about 5 seconds, about 10 seconds, about 15 seconds, about 20 seconds, about 30 seconds, about 45 seconds, or about 60 seconds.

The systems, methods, and devices can be used for determining a clinically-significant change in PA pressure in a subject by detecting RV motion based on microwave Doppler sensing. These methods rely on motion-associated Doppler shift sensing via a quadrature radar transceiver placed over the surface of a chest of a subject. Unlike methods or devices that detect cardiac motion based on whole body motion from received signals at the surface of the skin of a subject (e.g., via a ballistocardiogram), systems described herein detect spatial motions of the heart, portions of the heart, or individual chambers of the heart that arise from received signals at the surface of the heart.

A mobile device described herein can be used in a subject's home without clinical intervention. The device described herein can detect heart motion in a subject continuously and non-invasively. The device can be worn by the subject, attached to the subject, mounted, stationary, or otherwise positioned in a configuration that is convenient for outpatient use and effective for signal transmission and detection.

Doppler radar sensing is widely used for speed sensing, weather forecasting, and other applications for motion sensing. Doppler radar sensing also has utility in biomedical applications to acquire vital signs in a non-contact fashion. For example, the modulated phase shift associated to periodic cardiopulmonary motions reflected on the surface of a subject's chest can be processed to yield physiological information from the subject, such as heart rate, respiratory rate, tidal volume, pulse transit time, and cardiopulmonary motion amplitude. However, microwave Doppler radar vital sign sensing based on reflections arising from the chest surface only indirectly monitors cardiopulmonary motions. Signals arising from chest surface motions are induced by periodically pounding of the heart in the inner chest or by ribcage expansion and contraction as a result of respiration. Microwave signals used to probe these signals are largely reflected off the surface of the chest wall and only a very small portion reach the actual organ of interest (i.e., the heart). Thus, methods of directly monitoring the heart, for example, by detecting reflections arising from the surface of the heart itself, can be more useful for determining spatial changes of the heart.

Described herein are systems and devices containing a body-coupled probe coupled to a Doppler radar transceiver, which transmits low-power radio wave signals into the chest cavity and onto the surface of the heart wall. The mechanical contraction and expansion of the heart muscle creates a Doppler shift due to the Doppler effect. Thus, upon transmission of electromagnetic radiation to the heart, the motion of the heart wall can be modulated into a reflected signal.

The motions of the surface of the heart can be quantitatively monitored along the line-of-sight probed by a radar beam. Specifically, a Doppler radar system can probe the surface motion of different chambers of the heart subject, i.e., the right or left atria and right or left ventricles. In heart failure patients, the system provides the possibility to monitor changes in the volume (owing to the change in extent of movement) of the ventricles and atria as a result of decompensation following initial successful treatment. Monitoring of the degree of movement of the RV, in particular, can be used to determine changes in PA pressure. Reduced movements can be correlated with elevated pressure. In this manner, heart chamber size variations resulting from heart failure-related abnormalities associated with elevated PA pressure can be determined. By properly aligning the probing location and angle, i.e., placing the probe in contact to sternum with radar beam irradiating into the thoracic cavity, Doppler radar can provide a sensitive, non-invasive method to monitor PA pressure changes.

Cardiac Motion Monitoring Device

Patients with congestive heart failure often decompensate due to fluid retention, which can be due to excessive fluid intake, reduced renal excretion of salt and water, or decreased renal function. As patients decompensate over time, usually days to weeks, this increased volume causes interstitial and alveolar fluid accumulation resulting in elevated pulmonary arterial pressure. Elevated pulmonary pressure can be monitored using invasive devices (e.g., CardioMems®, which requires implantation of a catheter to the pulmonary artery). However, these devices require percutaneous insertion with attendant costs and risks, thus limiting their utility for monitoring PA pressure changes. The RV of the heart can respond to changes in PA pressure, e.g., when PA pressure is elevated. Serial detection of mechanical motions of the RV can reflect changes in PA pressure. This information can be used to infer conditions that are treatable with medications or other therapeutic interventions, thereby reducing morbidity and hospitalizations.

A device described herein can be worn by a subject to measure PA pressure changes in various environments. PA pressure changes can be monitored in a healthcare setting, such as a clinic, hospital, or doctor's office, or in a place away from the clinic, for example, at home, school, or any place where the subject wishes to wear the device. A device described herein can also be used during performance of everyday activities, for example, while driving a car, doing daily errands, exercising, shopping, or during periods of rest or sleep. The device described herein can use, for example, electromagnetic signals to determine the motion of a subject's heart to monitor clinically-significant changes to the PA pressure of a subject.

A device described herein can be used during short-term visits to a clinic, hospital, or doctor's office. The device can also be used by a subject during an in-patient visit to a hospital, or while a subject is recovering in a hospital, but needs the freedom to be ambulatory.

FIG. 1 illustrates a device 101 to determine the motion of the heart of a subject. The transmitter 102 of the transceiver circuit 109 generates a signal 108 that is routed to an antenna 105 via the duplexer 104. A signal 108 can then propagate from the antenna 105 to an object of interest 106, such as a heart or a portion thereof. The signal 108 can be, for example, pulsed or continuous. In some embodiments, the signal 108 is electromagnetic radiation such as a radio wave, an electromagnetic signal, or a wavelength or frequency of the electromagnetic spectrum. In some embodiments, the signal 108 is a wave of energy having a frequency that is from 800 MHz to 3 GHz. In some embodiments, the transmitted signal is not an electrical current. After transmission of the signal 108 to the object of interest 106, a corresponding signal 107 is reflected off the object of interest 106. The reflected signal 107 is received by the antenna 105 and routed to the receiver 103 via the duplexer 104.

Figure 2:
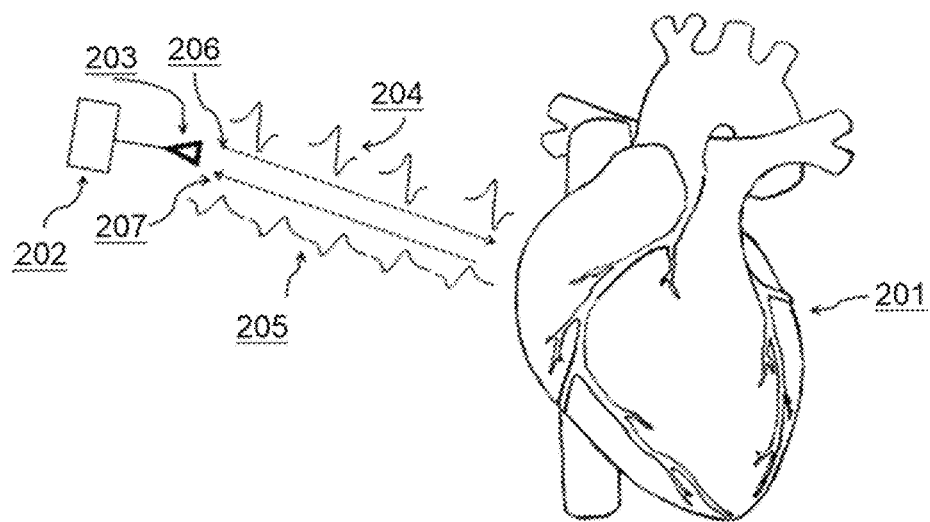
FIG. 2 depicts a function of a representative device of the invention.

FIG. 2 depicts a function of an example device of the invention. The device 202 comprises an antenna 203 that is positioned in proximity to, for example, a human heart 201. The antenna 203 can transmit 206 a signal 204 to the heart 201. The transmitted signal 204 reflects off of, for example, the muscle tissue at the surface of the heart to produce a reflected signal 205. The reflected signal 205 is then received 207 by the device 202 and processed for analysis. In some embodiments, a device described herein is positioned to a position that is suitable for transmission of the wave of energy to the heart of the subject. For example, the device can be positioned to be in contact with the subject's body, in contact with the subject's clothing, in contact with a chest of a subject, in contact with the subject near a sternum of the subject, in proximity to a chest of the subject, or in proximity to a sternum of the subject.

Figure 3:
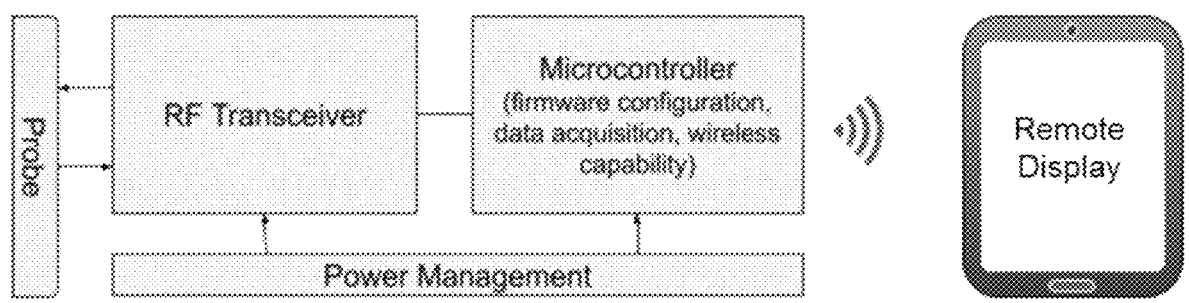
FIG. 3 depicts a representative system of the invention.

FIG. 3 illustrates a representative system of the invention for non-invasive monitoring of PA pressure changes. The system contains a probe, a radiofrequency (RF) transceiver comprising a transmitting antenna and a receiving antenna, a microcontroller, a power management module, and optionally, a remote display platform. The transceiver can be attached to the subject's body in direct contact with or without clothing in between. The transmitting antenna of the transceiver generates RF signals and transmits the RF signals. The RF signals can be duty-cycled or continuous. The receiving antenna of the transceiver receives reflected signals from the heart in response to the transmitted signals. The reflected signals from RV of the heart can be used to extract parameters that are correlated to size variations of RV of the heart. In some embodiments, the transceiver can perform signal conditioning or filtering when necessary. The microcontroller manages system configuration, data acquisition, and data transfer.

Figure 4:
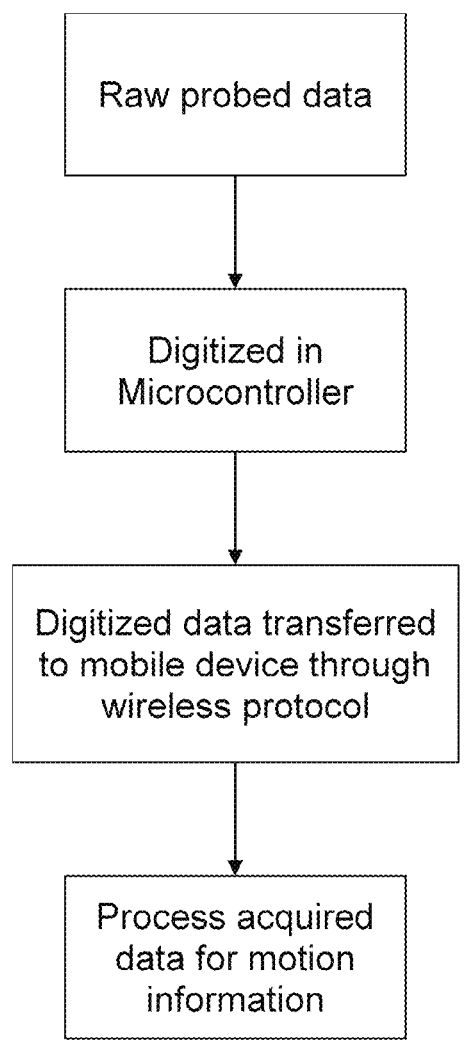
FIG. 4 illustrates the process of data acquisition and data transmission using a representative device of the invention.

FIG. 4 illustrates the process of data acquisition and data transmission using a device described herein. Raw probed data received from a RF transceiver are digitized by the microcontroller and wirelessly transferred to a mobile platform for real-time display and signal processing. Signal data can be transferred to a remote device, such as a display or a processor, through electronic cables or wireless methods. The raw data can also be stored locally in the memory on the monitor and downloaded to mobile platform when necessary.

Figure 12:
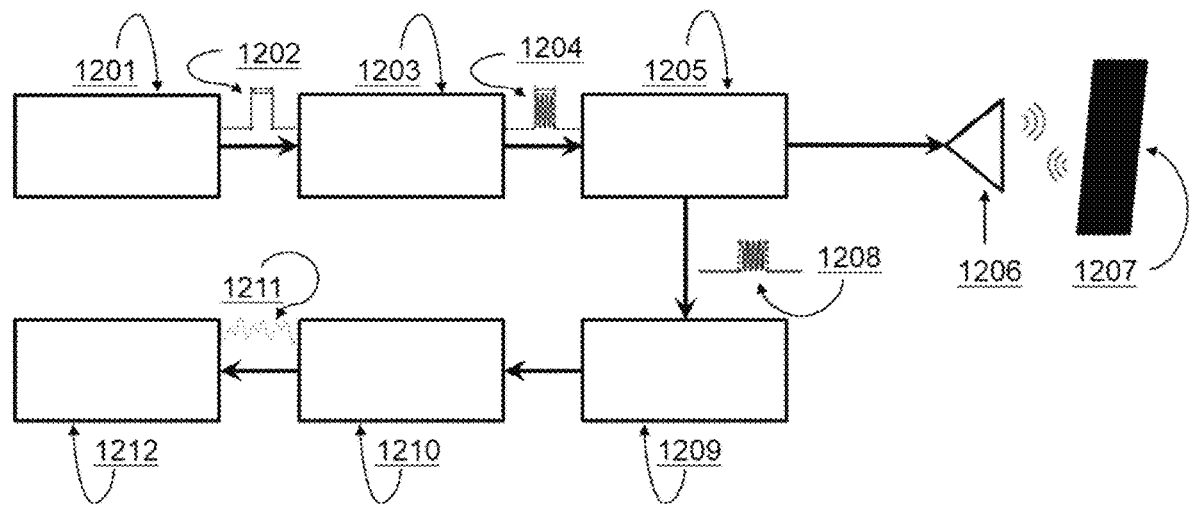
FIG. 12 depicts a representative device of the invention.

FIG. 12 illustrates an embodiment of a device to determine the motion of the heart of a subject. The pulse generator 1201 generates a pulse 1202 that is routed through a pulsed sine wave generator 1203 to generate a pulse waveform 1204. The pulse waveform 1204 is then routed to the antenna 1206 via the duplexer 1205. The pulse waveform 1204 can then propagate from the antenna 1206 to a target 1207, such as a heart of portion thereof. In some embodiments, the pulse waveform 1204 is electromagnetic radiation such as a radio wave, an electromagnetic signal, a wavelength or frequency of the electromagnetic spectrum, a wavelength of light, or a photon. After transmission of the pulse waveform 1204 to target 1207, a corresponding pulse waveform is reflected off the target 1207, such as the heart. The reflected pulse waveform is received by the antenna 1206 and routed to the mixer 1209 via the duplexer 1205, which converts the reflected pulse waveform into a duplexed waveform 1208. The duplexed waveform 1208 is propagated from the mixer 1209 to an amplifier and filters 1210 to generate the filtered waveform 1211. The filtered waveform 1211 is then propagated to the signal processing and display unit 1212.

Figure 13:
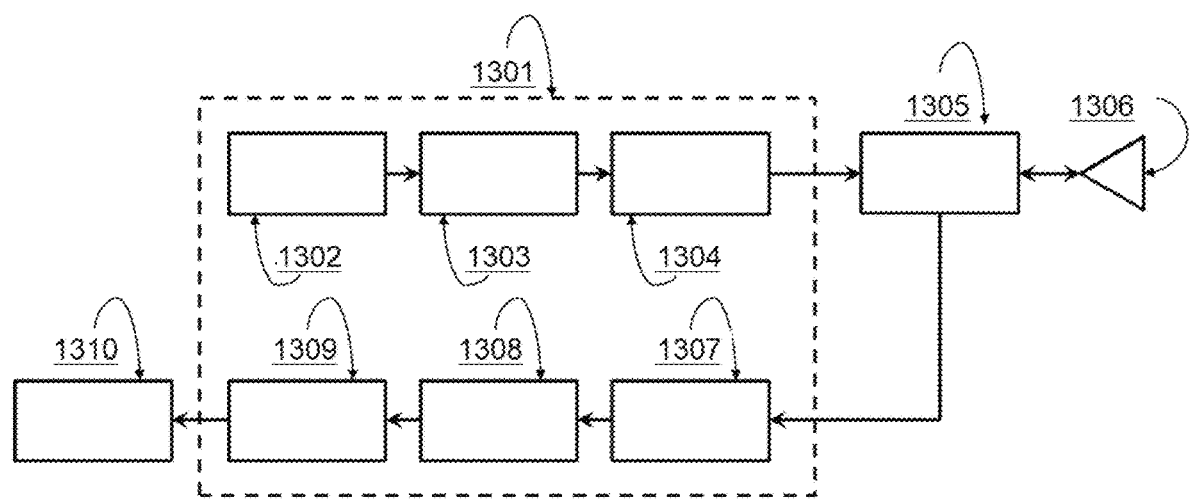
FIG. 13 depicts a representative device of the invention.

FIG. 13 illustrates an embodiment of a device described herein for determining the motion of the heart or a portion thereof. Within a printed circuit board (PCB) 1301, a voltage-controlled oscillator 1302 generates a waveform. The waveform is then propagated through a splitter 1303 and a first amplifier 1304 to a circulator 1305. The waveform is then carried from the circulator 1305 to an antenna 1306. A reflected waveform is then carried from the antenna 1306 to the circulator 1305. The waveform is then propagated to a second amplifier 1307. The waveform is then filtered through a bandpass filter 1308. The filtered waveform is then decoded using a quadrature demodulation chip 1309. The decoded waveform is then transmitted to a signal acquisition unit 1310.

An antenna or transceiver of a system or device disclosed herein transmits and/or receives electromagnetic radiation such as a radio wave, an electromagnetic signal, a wavelength or frequency of the electromagnetic spectrum, a wavelength of light, or a photon.

In some embodiments, a device described herein comprises a radar sensing system. Non-limiting examples of the types of radar that can be used in the device include quadrature Doppler radar, ultrawide bandwidth radar, continuous wave Doppler radar, pulsed Doppler radar, frequency-modulated continuous wave radar, or pseudorandom code-modulated continuous wave radar.

In some embodiments, multiple radar sensors can be used to increase the accuracy of the cardiac measurements. Multiple radar sensors also measure heart motion profiles from different positions of view and generate a multi-dimensional data set that can be inverted to determine the motion of the heart in two dimensions. This method can provide accurate measurements by reducing the effect of random movement or misalignment of individual radar sensors.

In some embodiments, a device described herein comprises a monostatic radar architecture in which a single antenna is used for both transmission and reception. In some embodiments, a device described herein comprises a duplexer, which can separate transmitted and received signals when one antenna is used for both transmission and reception. In a monostatic radar system, generated signals are passed directly to the antenna, while received signals from the antenna are routed to the receiver portion. A duplexer can provide isolation between the transmit and receive paths, thereby allowing for one antenna to perform both functions.

In some embodiments, a device described herein comprises a bistatic radar architecture. In a device comprising a bistatic radar architecture, two antennas are spatially separated for the transmit and receive paths.

Non-limiting examples of antennae that can be used in the device include an isotropic radiator, a dipole antenna, a Yagi-Uda antenna, a random wire antenna, a horn antenna, a parabolic antenna, and a patch antenna. In some embodiments, the antenna can be detachable or removable from the device. In some embodiments, the antenna can be interchangeable or exchangeable for a different antenna, for example, an antenna of a differing strength. The antenna can be placed, for example, inside, outside, in proximity to, adjacent to, on top of, or below the device.

In some embodiments, the device can be used to determine whether the subject has a condition associated with elevated PA pressure based on reduced RV wall motion. Non-limiting examples of conditions associated with elevated PA pressure include pulmonary hypertension, pulmonary arterial hypertension (PAH), cardiac arrest, ischemic cardiomyopathy, heart failure, congestive heart failure (CHF), decompensated heart failure (DHF), decompensated chronic heart failure, and acute decompensated heart failure (ADHF).

A device described herein can comprise a computer system receives data associated with a signal reflecting off a subject's heart. The data that is received by the computer system can then be compared by a processor of the computer system to a reference to determine a clinically-significant change in PA pressure in the subject. The received data can also be compared by the processor of the computer system to a reference to determine a trend in an average magnitude motion of the heart of the subject over a time period of detection. The received data can also be compared by the processor of the computer system to a reference to determine whether the subject has a heart failure condition. Non-limiting examples of references that can be used by the computer system include past measurements from the subject, measurements from a healthy subject (having normal PA pressure), statistical averages of the symptom being measured, and reference texts. The computer system can then output a result of the determination. In some embodiments, the processor is located in a housing common to the source of the signal in the device (e.g. a transceiver or antenna). In some embodiments, the processor is not located in a housing common to the source of the signal in the device.

In some embodiments, the device comprises a processor coupled to a transmitter configured to transmit data from the device to a remote location, for example, a hospital, clinic, or doctor's office. The transmitter can be configured to transmit data wirelessly, for example, via Bluetooth®, wireless networks, cell phone networks, a cloud network, or the internet. For example, the device can use Bluetooth® to connect to an analysis device, including but not limited to, a mobile device, tablet, cellular phone, or computer system. In some embodiments, the transmission is wired. The processor can be configured to transmit data to a plurality of receivers in a plurality of geographic locations. In some embodiments, the processor can transmit data over a distance of about 1 mile, about 2 miles, about 3 miles, about 4 miles, about 5 miles, about 6 miles, about 7 miles, about 8 miles, about 9 miles, or about 10 miles. In some embodiments, the processor can transmit data over a distance of at least 10 miles. In some embodiments, the processor can transmit data over a distance of at least 50 miles. In some embodiments, the device comprises a Global Positioning System (GPS).

A device described herein can be, or cannot be, worn by a subject. In some embodiments, the device can be positioned in a position suitable for transmission of the wave of energy to the heart of the subject, for example, in contact with the subject's body, in contact with the subject's chest, or in contact with the subject near the subject's sternum. In some embodiments, the device can be fitted to the subject in proximity to the subject's chest or in proximity to the subject's sternum.

In some embodiments, the device can be attached to a subject's body using, for example, a chest strap, a chest vest, an arm band, a wrist band, a headband, a belt, an adhesive tape, or glue. A device described herein can be embedded in a subject's clothing, for example, an undergarment, a bra, a shirt, a jacket, or a sweater. A device described herein can be embedded in a wearable device, for example, a watch, an earring, a necklace, a ring, or a bracelet. The device can also be unattached from the subject's body. A device described herein can be attached to, for example, a wall, a headboard, a bed, a mirror, a nightstand, a chair, or other furniture in proximity to the subject. The device can be embedded in, for example, a mattress, a pillow, a comforter, or a sofa.

A device described herein can be, or cannot be, at a distance from a subject. The distance between the device and the subject can be zero (i.e., on the surface of the subject's body or clothing), at least about 1 centimeter (cm), at least about 2 cm, at least about 3 cm, at least about 4 cm, at least about 5 cm, at least about 6 cm, at least about 7 cm, at least about 8 cm, at least about 9 cm, at least about 10 cm, at least about 11 cm, at least about 12 cm, at least about 13 cm, at least about 14 cm, at least about 15 cm, at least about 16 cm, at least about 17 cm, at least about 18 cm, at least about 19 cm, at least about 20 cm, at least about 21 cm, at least about 22 cm, at least about 23 cm, at least about 24 cm, at least about 25 cm, at least about 26 cm, at least about 27 cm, at least about 28 cm, at least about 29 cm, at least about 30 cm, at least about 31 cm, at least about 32 cm, at least about 33 cm, at least about 34 cm, at least about 35 cm, at least about 36 cm, at least about 37 cm, at least about 38 cm, at least about 39 cm, at least about 40 cm, at least about 41 cm, at least about 42 cm, at least about 43 cm, at least about 44 cm, at least about 45 cm, at least about 46 cm, at least about 47 cm, at least about 48 cm, at least about 49 cm, at least about 50 cm, at least about 60 cm, at least about 70 cm, at least about 80 cm, at least about 90 cm, at least about 1 meter (m), at least about 2 m, at least about 3 m, at least about 4 m, at least about 5 m, at least about 6 m, at least about 7 m, at least about 8 m, at least about 9 m, at least about 10 m, at least about 15 m, or at least about 20 m.

The distance between the device and the subject can be at most about 1 centimeter (cm), at most about 2 cm, at most about 3 cm, at most about 4 cm, at most about 5 cm, at most about 6 cm, at most about 7 cm, at most about 8 cm, at most about 9 cm, at most about 10 cm, at most about 11 cm, at most about 12 cm, at most about 13 cm, at most about 14 cm, at most about 15 cm, at most about 16 cm, at most about 17 cm, at most about 18 cm, at most about 19 cm, at most about 20 cm, at most about 21 cm, at most about 22 cm, at most about 23 cm, at most about 24 cm, at most about 25 cm, at most about 26 cm, at most about 27 cm, at most about 28 cm, at most about 29 cm, at most about 30 cm, at most about 31, at most about 32 cm, at most about 33 cm, at most about 34 cm, at most about 35 cm, at most about 36 cm, at most about 37 cm, at most about 38 cm, at most about 39 cm, at most about 40 cm, at most about 41 cm, at most about 42 cm, at most about 43 cm, at most about 44 cm, at most about 45 cm, at most about 46 cm, at most about 47 cm, at most about 48 cm, at most about 49 cm, at most about 50 cm, at most about 60 cm, at most about 70 cm, at most about 80 cm, at most about 90 cm, at most about 1 meter (m), at most about 2 m, at most about 3 m, at most about 4 m, at most about 5 m, at most about 6 m, at most about 7 m, at most about 8 m, at most about 9 m, at most about 10 m, at most about 15 m, or at most about 20 m.

A device described herein can be, or cannot be, in contact with a subject's skin or clothing. The device can be placed in proximity to, for example, the torso, the chest, the sternum, the heart, or the thoracic cavity of a subject. The device can be placed directly on, for example, the chest, the sternum, or the thoracic cavity of a subject. In some embodiments, the device can be placed on the center of the chest, the upper part of the chest, the lower part of the chest, the left part of the center of the chest, or the right part of the center of the chest of a subject. In some embodiments, the device can be placed on the back of a subject, for example, in line with, above, below, left, or right of the sternum. In some embodiments, the device can be placed in front of, for example, the torso, the chest, the sternum, or the thoracic cavity of a subject. In some embodiments, the device can be placed on a subject while the subject is in an upright position, a supine position (torso facing upward), a prone position (torso facing downward), while sitting, or while standing.

Figure 5:
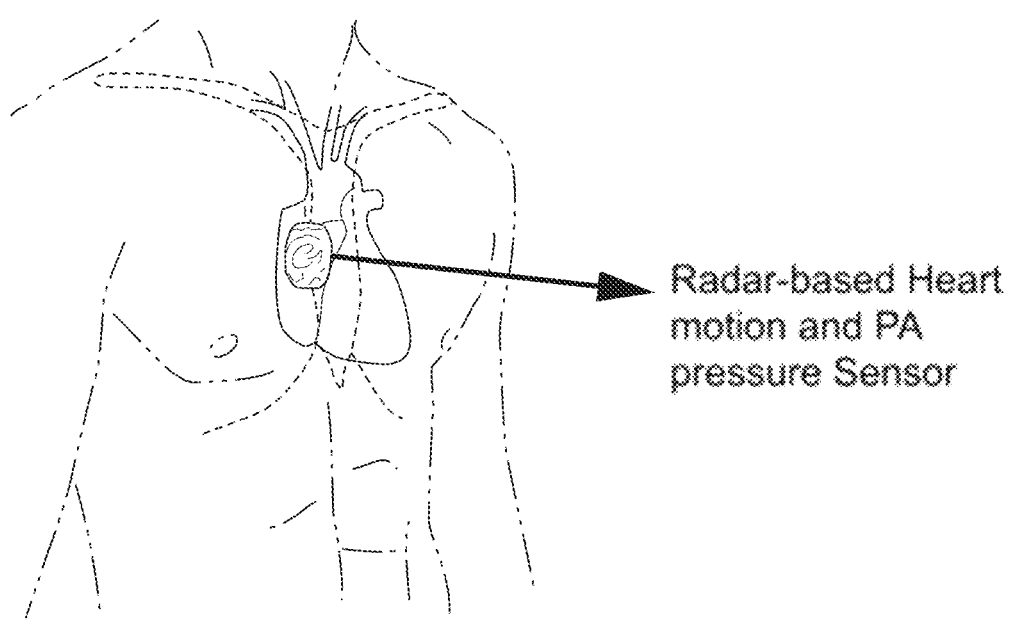
FIG. 5 illustrates an example placement of a representative device of the invention.

FIG. 5 illustrates placement of the device to the sternum area of a subject and in contact with the subject. The sternum is the large, flat bone in the middle of the upper torso that connects the left and right halves of the rib cage. Through the sternum of the chest, electromagnetic signals can be transmitted to the thoracic cavity and onto the surface of the heart, for example, the surface of a portion or chamber of the heart.

A device described herein can be used by a subject holding breath. In some embodiments, the device can be used by a subject breathing normally.

A device described herein can be used by a subject hourly, daily, weekly, monthly, yearly, occasionally, frequently, continuously, or chronically. A device described herein can be used by a subject as needed based on a condition of the subject, upon a doctor's recommendation, as desired by the subject, as required to monitor the condition of the subject properly, or for diagnostic or research purposes.

In some embodiments, a device described herein has an average output power of about 1 µW, about 2 µW, about 3 µW, about 4 µW, about 5 µW, about 6 µW, about 7 µW, about 8 µW, about 9 µW, about 10 µW, about 20 µW, about 30 µW, about 40 µW, about 50 µW, about 60 µW, about 70 µW, about 80 µW, about 90 µW, about 100 µW, about 200 µW, about 300 µW, about 400 µW, about 500 µW, about 600 µW, about 700 µW, about 800 µW, about 900 µW, about 1 mW, about 2 mW, about 3 mW, about 4 mW, about 5 mW, about 6 mW, about 7 mW, about 8 mW, about 9 mW, about 10 mW, about 15 mW, about 20 mW, about 25 mW, about 30 mW, about 35 mW, about 40 mW, about 45 mW, about 50 mW, about 60 mW, about 70 mW, about 80 mW, about 90 mW, or about 100 mW.

A device described herein can produce pulses of electromagnetic waves. The duration of the pulses can be about 1 ps, about 2 ps, about 3 ps, about 4 ps, about 5 ps, about 6 ps, about 7 ps, about 8 ps, about 9 ps, about 10 ps, about 20 ps, about 30 ps, about 40 ps, about 50 ps, about 60 ps, about 70 ps, about 80 ps, about 90 ps, about 100 ps, about 110 ps, about 120 ps, about 130 ps, about 140 ps, about 150 ps, about 160 ps, about 170 ps, about 180 ps, about 190 ps, about 200 ps, about 250 ps, about 300 ps, about 350 ps, about 400 ps, about 450 ps, about 500 ps, about 600 ps, about 700 ps, about 800 ps, about 900 ps, about 1 ns, about 2 ns, about 3 ns, about 4 ns, about 5 ns, about 6 ns, about 7 ns, about 8 ns, about 9 ns, about 10 ns, about 20 ns, about 30 ns, about 40 ns, about 50 ns, about 60 ns, about 70 ns, about 80 ns, about 90 ns, about 100 ns, about 200 ns, about 300 ns, about 400 ns, about 500 ns, about 600 ns, about 700 ns, about 800 ns, about 900 ns, or about 1 µs. The repetition rate of the pulses can be about 0.1 MHz, about 0.2 MHz, about 0.3 MHz, about 0.4 MHz, about 0.5 MHz, about 0.6 MHz, about 0.7 MHz, about 0.8 MHz, about 0.9 MHz, about 1 MHz, about 2 MHz, about 3 MHz, about 4 MHz, about 5 MHz, about 6 MHz, about 7 MHz, about 8 MHz, about 9 MHz, about 10 MHz, about 15 MHz, about 20 MHz, about 25 MHz, about 30 MHz, about 35 MHz, about 40 MHz, about 45 MHz, about 50 MHz, about 60 MHz, about 70 MHz, about 80 MHz, about 90 MHz, or about 100 MHz.

Non-limiting examples of device shape include a cube, a sphere, a cylinder, a square, a rectangle, and a circle. A device described herein can have a height (H), width (W), and depth (D), each independently of about 0.05 inches, about 0.1 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch. In some embodiments, the device is a cube. In some embodiments, the device has dimensions of about 2 inches by about 2 inches by about 1 inch. In some embodiments, the device has dimensions of about 2.25 inches by about 2.25 inches by about 1.75 inches. In some embodiments, the device has dimensions of about 1 inch by about 1 inch by about 0.2 inch. In some embodiments, the device has dimensions of about 2 inches by about 1 inch by about 0.5 inch.

Non-limiting examples of materials that can be used in the manufacture of the device include polyvinyl chloride, polyethylene, polypropylene, polystyrene, polyurethane, polyethylene terephthalate, polycarbonate, silicone, and combinations thereof. Further non-limiting examples of materials that can be used in the manufacture of the device include steel, low-carbon steel, medium-carbon steel, high-carbon steel, aluminum, brass, copper, lead, magnesium, nickel, titanium, zinc, and combinations thereof. Additional non-limiting examples of materials that can be used in the manufacture of the device include copper wire, aluminum wire, XHHW wire, THWN wire, and THEN wire.

Non-limiting examples of chips that can be used in the manufacture of the device include dynamic random access memory chips, microprocessors, application specific integrated circuits, digital signal processors, programmable memory chips, and combinations thereof.

Non-limiting examples of semiconductors that can be used in the manufacture of the device include diamond, silicon, germanium, tin, silicon carbide, selenium, tellurium, boron nitride, zinc oxide, copper (I) oxide, and combinations thereof.

In some embodiments, the device has a total mass of less than about 100 grams. The total mass of the device can be about 1 gram, about 2 grams, about 3 grams, about 4 grams, about 5 grams, about 6 grams, about 7 grams, about 8 grams, about 9 grams, about 10 grams, about 15 grams, about 20 grams, about 25 grams, about 30 grams, about 35 grams, about 40 grams, about 45 grams, about 50 grams, about 60 grams, about 70 grams, about 80 grams, about 90 grams, about 100 grams, about 110 grams, about 120 grams, about 130 grams, about 140 grams, about 150 grams, about 200 grams, about 250 grams, about 300 grams, about 350 grams, about 400 grams, about 450 grams, about 500 grams, about 550 grams, about 600 grams, about 650 grams, about 700 grams, about 750 grams, about 800 grams, about 850 grams, about 900 grams, about 950 grams, or about 1000 grams.

Any tool, interface, engine, application, program, service, command, or other executable item can be provided as a module encoded on a computer-readable medium in computer-executable code. In some embodiments, described herein is a computer-readable medium encoded therein computer-executable code that encodes a method for performing any action described herein, wherein the method comprises providing a system comprising any number of modules described herein, each module performing any function described herein to provide a result, such as an output, to a user.

Applications of a Device of the Invention

The device described herein can be used to monitor the cardiac activity of a subject to infer a clinically-significant PA pressure change. The monitoring can detect the motion of the subject's heart, for example, the motion of a portion of the heart, a chamber of the heart, a right ventricle of the heart, a left ventricle of the heart, s right atrium of the heart, or a left atrium of the heart. The device can also detect, for example, an upward or downward trend associated with a movement of the RV, the relative position of a portion of the heart as compared to the rest of the heart, a movement of the left atrium, a movement of the right atrium, a movement of the left ventricle, a movement of the right ventricle, a change in a dimension of the heart, a change in a dimension of a chamber of the heart, a change in a dimension of the left atrium, a change in a dimension of the right atrium, a change in a dimension of the left ventricle, a change in a dimension of the right ventricle, the heart rate, the respiratory rate, the pattern of the heart rate, the regularity of the heartbeat, the irregularity of the heartbeat, the strength of the heartbeat, the intensity of the heartbeat, the position of the heart muscles, the velocity of the heart muscles, the relative strength of diastole, the relative strength of systole, the sinus rhythm of the atria, the sinus rhythm of the ventricles, thoracic fluid content (TFC), the blood oxygen saturation level, ejection fraction (EF), cardiac output, and stroke volume (SV). Movement of a chamber of a heart can be associated with expansion or contraction.

The device described herein can obtain and record measurements, for example, when the subject is at rest, in motion, while performing light exercise, while performing heavy exercise, walking, running, jogging, biking, or sleeping. Measurements taken during these times can be compared to readings taken during other times to determine a clinically-significant PA pressure change in the subject.

A subject can be, for example, an elderly adult, an adult, an adolescent, a child, a toddler, or an infant. A subject can be, for example, an individual with a heart condition or an individual without a heart condition. A subject can be a patient.

The device described herein can be used to monitor patients with heart failure who have elevated PA pressures due to decompensation and measure RV motion as a surrogate/reflection of PA pressure changes. Pulmonary hypertension can be caused by, for example, heart failure, blood clots, blood disorders, scarring of the heart muscle from a previous heart attack, cardiomyopathy, diabetes, HIV, hyperthyroidism, stress, smoking, medication side effects (e.g., chemotherapy-induced cardiotoxicity), liver disease, lung disease, emphysema, chronic bronchitis, pulmonary fibrosis, lupus, scleroderma, rheumatoid arthritis, autoimmune diseases, sleep apnea, or illicit drug use. Major symptoms of pulmonary hypertension include, for example, chest pressure, chest pain, shortness of breath (dyspnea), fatigue, dizziness, heart palpitations, swelling of the ankles or legs (edema), bluish coloring of the lips and skin (cyanosis), fainting, and syncope.

A device described herein can be used to determine, observe, record, time, track, or calculate PA pressure changes in a subject based on a motion of a subject's heart, or a portion thereof. For example, PA pressure changes can be determined based on a motion of RV of the heart. The motion can be an expansion or contraction of a chamber of the heart. Decreasing contraction intensities of a heart chamber can indicate increases in PA pressure. Similarly, increasing contraction intensities of a heart chamber can indicate decreases in PA pressure. The PA pressure changes can be determined over any time period by an analysis of data comparing episodes of a normal or elevated PA pressure to the subject's PA pressure or to a reference heartbeat. Thus, the motion of a heart chamber can be used to determine whether the PA pressure is increasing, decreasing, or remaining constant over time.

As described herein, a "subject" or "patient" is an individual, such as an animal or human. Thus, a "subject" or "patient" can include domesticated animals (e.g., cats, dogs, etc.), livestock (e.g., cattle, horses, pigs, sheep, goats, etc.), laboratory animals (e.g., mouse, rabbit, rat, guinea pig, etc.), birds, mammals, primates, or humans. A subject can exhibit a disease or condition, or a symptom thereof. Non-limiting examples of a disease or condition can include hypertension, pulmonary hypertension, PAH, decompensation, heart failure, congestive heart failure, congenital heart disease, valvular heart disease, cardiomyopathy, myocarditis, cardiac arrhythmia, diabetes, hyperlipidemia, obesity, anemia, sleep apnea, HIV, hyperthyroidism, hypothyroidism, hemochromatosis, and amyloidosis. A subject can exhibit a heart failure condition, including but not limited to, decompensated heart failure, acute decompensated heart failure, congestive heart failure, fluid accumulation in the heart, right-sided heart failure, left-sided heart failure systolic heart failure, diastolic heart failure, Stage A heart failure, Stage B heart failure, Stage C heart failure, and Stage D heart failure.

The device described herein can be used to monitor PA pressure changes in a subject undergoing an intervention for heart failure. The device described herein can be used to monitor PA pressure changes in a subject undergoing an intervention for heart failure. The intervention can involve pharmacological agents, devices that are, or are not, implanted in the subject to modulate the heartbeat, surgery, and combinations thereof. The device can be used to determine whether the intervention modulates PA pressure by comparing readings taken before and after administration of the intervention, or during the course of therapy. Non-limiting examples of interventions used by a subject that can be monitored by systems and devices described herein include amiodarone, bepridil hydrochloride, disopyramide, dofetilide, dronedarone, flecainide, ibutilide, lidocaine, procainamide, propafenone, propranolol, quinidine, sotalol, tocainide, amlodipine, diltiazem, felodipine, isradipine, nicardipine, nifedipine, nimodipine, nisoldipine, verapamil, acebutolol, atenolol, betaxolol, bisoprolol, hydrochlorothiazide, carteolol, esmolol, metoprolol, nadolol, penbutolol, pindolol, timolol, warfarin, dalterparin, enoxaparin, heparin, tinzaparin, aspirin, ticlopidine, clopidogrel, dipyridamole, benazepril, captopril, enalapril, fosinopril, lisinopril, moexipril, perindopril, quinapril, ramipril, trandolapril, candesartan, eprosartan, irbesartan, losartan, temisartan, valsartan, sacubitril, amiloride, bumetanide, chlorothiazide, chlorthalidone, furosemide, indapamide, spironolactone, isosorbide dinitrate, nesiritide, hydralazine, minoxidil, lanoxin, atorvastatin, fluvastatin, lovastatin, pitavastatin, pravastatin, rosuvastatin, simvastatin, clofibrate, gemfibrozil, digoxin, adenosine, diphenhydramine, chlorpheniramine, clemastine, brompheniramine, hydroxyzine, cetirizine, fexofenadine, loratadine, dextroamphetamine, methamphetamine, methylphenidate, fenfluramine, dexfenfluramine, MDMA, cocaine, pseudoephedrine, albuterol, isoproterenol, salmeterol, isoetharine, phencyclidine, tranylcypromine, phenelzine, theophylline, aminophylline, caffeine, nortriptyline, amitriptyline, imipramine, desipramine, scopolamine, propantheline, atropine, cisapride, erythromycin lactobionate, pentamidine, chloroquine, amantadine, iloprost, epoprostenol, treprostinil sodium, sildenafil, tadalafil, selexipag, dobutamine, ambristentan, bosentan, macitentan, riociguat, a calcium channel blocker, a vasodilator, a blood vessel dilator, anticoagulants, a prostacyclin, an endothelin receptor antagonist (ERA), a phosphodiesterase (PDE)-5 inhibitor, a guanylate cyclase stimulator, a diuretic, radiofrequency ablation, transcatheter ablation, defibrillation, a pacemaker, an implantable cardioverter defibrillator, a inotropic agent, a beta blocker, an aldosterone antagonist, an ACE inhibitor, an angiotensin II receptor blocker (ARB), an angiotensin receptor-neprilysin inhibitors (ARNI), a heart pump medication, potassium, magnesium, a selective sinus node inhibitor, and combinations thereof.

The device described herein can be used to monitor PA pressure changes in a subject undergoing an intervention for a cancer, tumor, hyperproliferative disorder, or neoplasia. The intervention can comprise pharmacological agents, surgery, and combinations thereof. In some embodiments, the intervention is an intervention for a heart failure condition. Non-limiting examples of heart failure interventions include heart surgery and heart transplantation. The device can be used to determine whether the intervention modulates PA pressure by comparing readings taken before and after administration of the intervention, or during the course of therapy. Additional non-limiting examples of interventions used by a subject that can be monitored by systems and devices described herein include doxorubicin, adriamycin, capecitabine, gemcitabine, cytarabine, paclitaxel, docetaxel, cisplatin, carboplatin, oxaliplatin, 5-fluorouracil, chlorambucil, cyclophosphamide, busulfan, melphalan, arsenic trioxide, IL-2, methotrexate, trastuzumab, sunitinib, cetuximab, alemtuzumab, rituximab, thalidomide, amsacrine, dispeptide, and combinations thereof.

The device described herein can be used to monitor PA pressure changes in a subject using recreational or illicit drugs. The device can be used to determine whether the recreational drug use causes a PA pressure change by comparing readings taken in the presence and absence of drug use, or during the course of drug use. Non-limiting examples of recreational drugs used by a subject that can be monitored by systems and devices described herein include dextroamphetamine, methamphetamine, methylphenidate, fenfluramine, dexfenfluramine, MDMA, cocaine, phencyclidine, lysergic acid diethylamide, psilocybin, morphine, heroin, volatile inhalants, cannabis and combinations thereof.

Signals Suitable for Use

A heart motion monitoring system described herein can comprise a transmitter, a receiver, and an antenna. The transmitter can generate a signal that is radiated into a space containing an object of interest by the antenna. The signal can then be reflected off the object of interest, and a reflected signal can be detected by the receiver. The receiver can amplify the signal for conversion to, for example, visual or audio data. In some embodiments, the transmitter and the receiver are in a common housing. In some embodiments, the transmitter, the receiver, and the antenna are in a common housing.

Ultrasound involves the use of high frequency sound waves outside the range of human hearing to create images of, for example, organs and systems within the human body. Medical sonography is the practice of imaging organs within the body. Ultrasound images (sonograms) are made by sending a pulse of ultrasound into tissue using an ultrasound transducer. The sound reflects and echoes off parts of the tissue and this echo is recorded and displayed as an image to the operator.

The electromagnetic (EM) spectrum is a continuum of all the possible frequencies of electromagnetic radiation. Electromagnetic radiation can be described by physical properties including frequency, wavelength, and energy. The different regions of the EM spectrum, in decreasing order of wavelength and increasing order of frequency, include radio waves, microwaves, far infrared, near infrared, visible, ultraviolet, x-rays, gamma rays, and high-energy gamma rays.

Radio waves are generally propagated via the use of an antenna and can have wavelengths that range from hundreds of kilometers to a millimeter. Radio waves can be used for communication satellites, navigation systems, radio communication, broadcasting, and radar.

Microwaves have wavelengths that range from one meter to millimeters. Microwaves are used in spacecraft communication and radar technology. Some television and telephone communications are transmitted long distances by microwaves between ground stations and communications satellites. Microwaves can be absorbed by molecules that have dipole moments in liquids.

Infrared radiation is characterized by wavelengths that range from about a millimeter to several hundred nanometers (nm). Infrared energy is emitted or absorbed by molecules when changing rotational-vibrational movements. Infrared energy elicits vibrational modes in a molecule through a change in the dipole moment, making infrared a useful frequency range for study of these energy states for molecules. Most thermal energy emitted from objects at room temperature is infrared.

The visible region of the EM spectrum is the portion of the spectrum to which the human eye is most sensitive. Electromagnetic radiation with wavelengths of between 380 and 760 nm is detectable by the human eye and perceived as visible light.

Ultraviolet (UV) radiation typically has wavelengths between 100 and 400 nm. UV light can be found in sunlight and has the potential to damage biological molecules due to its ability to alter chemical bonds. UV rays having very short wavelengths can ionize molecules.

X-rays have wavelengths in the range of about one to tenths of a nanometer. X-rays have the ability to penetrate through relatively thick objects without much scattering or absorption, thus making them useful for imaging visually opaque objects. X-rays are widely used in medical radiography and airport security scanners.

Gamma rays have extremely short wavelengths and a very high frequency. Natural sources of gamma rays include decay from naturally occurring radioisotopes. Gamma rays are also found in space as a result of supernova explosions. Due to their high energy, gamma rays are highly penetrating and can diffuse throughout the human body and cause radiation sickness.

Radar (radio detection and ranging) is a system that can use radio waves or microwaves to determine the range, altitude, speed, and direction of objects. Radio waves are a portion of the electromagnetic spectrum and are characterized by low frequency and long wavelengths. A radar system can use radio waves as a mechanism for the detection of objects.

Ultra-wideband (UWB) radar systems can use radio waves to transmit information spread over large bandwidths, for example, greater than 500 MHz. UWB radar systems can accomplish this task via pulse-modulation of the signal, in that UWB transmissions transmit information by generating radio waves at specific time intervals over a large bandwidth. Non-UWB transmissions can employ continuous signaling in which only the frequency, power level, or phase of the wave, but not the time interval, is changed.

Doppler radar utilizes the Doppler effect to produce velocity data about objects at a distance. Doppler radar can beam a microwave signal toward a desired target and listen for a reflection. This process allows for analysis of how the object's motion alters the frequency of the returned signal motion, and provides data about the object's velocity.

Continuous wave Doppler radar transmits a continuous wave of radio wave energy, allowing for the determination of an object's velocity without providing any range or distance data. Frequency-modulated continuous wave (FMCW) Doppler radar differs from continuous wave Doppler radar in that the frequency of the transmitted signal can be varied, allowing for measurements of an object's distance. Use of pseudorandom code modulated continuous wave radar can provide further refinement as to an object's distance and range. This refinement occurs via modulation of the transmitter's codes to meet frequency and range requirements for the objects of interest.

Pulsed Doppler radar uses pulse-timing techniques and the Doppler effect to determine the distance of an object. Pulsed Doppler systems differ from continuous wave systems by sending short pulses of radio energy rather than a continuous transmission of radio energy to an object. The range of an object is determined by the measuring the elapsed time between pulses sent to and reflected off the object.

EXAMPLES

Example 1. Analysis of Signal Loss Inside Human Tissues

Figure 6:
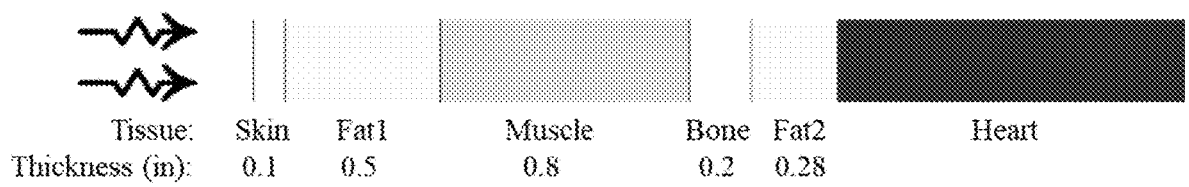
FIG. 6 illustrates the thickness of different tissues in the human body.

Monitoring of PA pressure changes in a subject using a device described herein can be optimized by positioning a device on, and in contact with, a subject for minimal signal loss in tissue. FIG. 6 illustrates the tissue thickness, in inches, of skin, fat, muscle, and bone anterior to the heart of a human. The amount of muscle tissue is relatively low. When radar signals were radiated through various tissues including skin, fat, muscle, and bone, the greatest loss of radar signal occurred in the muscle tissue, as demonstrated in FIG. 7.

Figure 7:
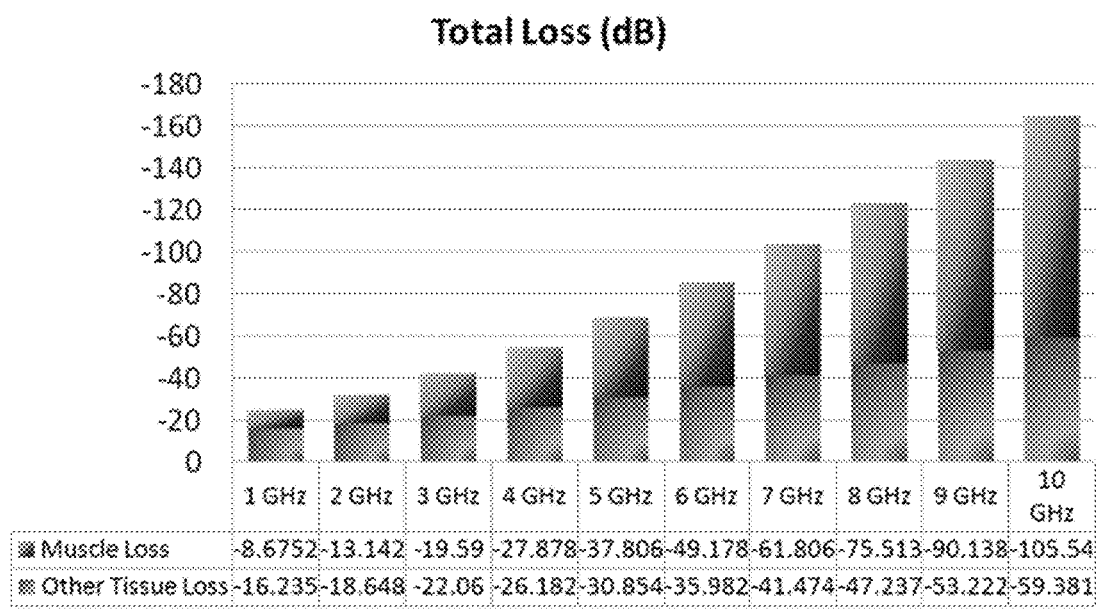
FIG. 7 depicts signal loss inside human tissue.

The loss of signal intensity positively correlated with the frequency of the signal, as shown in FIG. 7. When the frequency (GHz) of the signal was increased, the total loss of signal (dB) was most significant in the muscle, while other tissues accounted for only a minor portion of signal loss. This analysis further indicated that placement to the sternum, having minimal musculature, is an effective placement for the device. This placement allows for less signal loss and dispersion.

Example 2. Modeling Methodology

To calculate the interaction of transmitted signals generated by a device described herein with heart muscles, a three-dimensional full-wave simulation was employed. In this simulation, a three-dimensional model of the heart, or chest cavity, was used. First, the complexity of the model was reduced by removing portions of the chest cavity that do not move, and thus are not relevant for modeling the motion of the heart. Next, the heart model was imported into a wave simulation program to determine the signal received at the antenna in the form of a magnetic or electric field distribution. Finally, the extracted waveforms were fed into a circuit simulator to determine the correlation between the output signal and the motion of the heart.

Example 3. Computer Architectures

Figure 8:
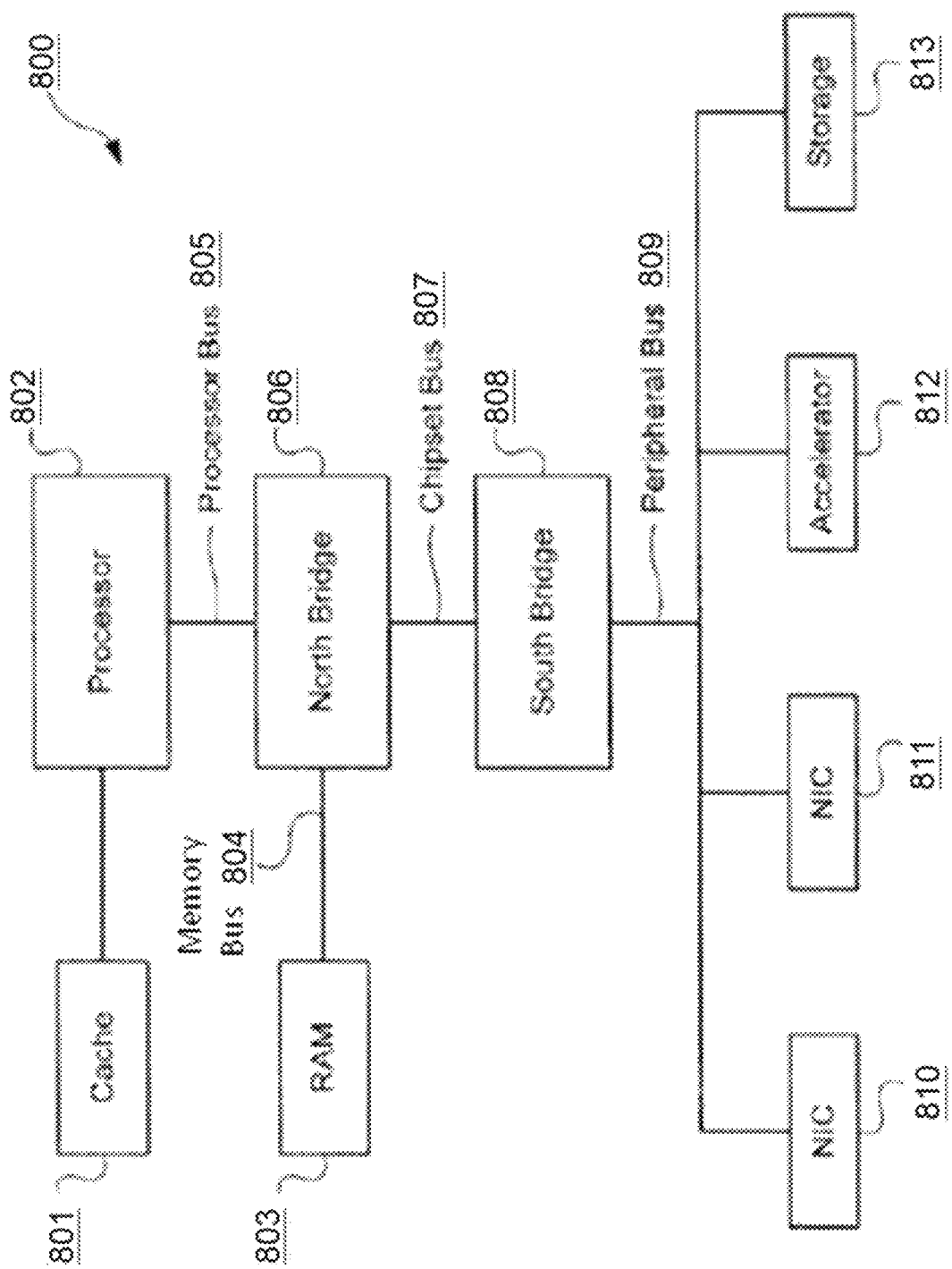
FIG. 8 is a diagram illustrating a first example architecture of a computer system that can be used in connection with example embodiments of the invention.

Various computer architectures are suitable for use with devices and systems described herein. FIG. 8 is a diagram illustrating a first example architecture of a computer system 800 that can be used in connection with example embodiments of the invention. As depicted in FIG. 8, the example computer system can include a processor 802 for processing instructions. Non-limiting examples of processors include: Intel Core i9® processor, Intel Core i7® processor, Intel Core i5® processor, Intel Core i3® processor, Intel Xeon® processor, AMD Opteron® processor, Samsung 32-bit RISC ARM 1176JZ(F)-S v1.0® processor, ARM Cortex-A8 Samsung S5PC100® processor, ARM Cortex-A8 Apple A4® processor, Marvell PXA 930® processor, or a functionally-equivalent processor. Multiple threads of execution can be used for parallel processing. In some embodiments, multiple processors or processors with multiple cores can be used, whether in a single computer system, in a cluster, or distributed across systems over a network comprising a plurality of computers, cell phones, tablet computing devices, watch based devices, wrist band devices, armband devices, or personal data assistant devices.

Data Acquisition, Processing and Storage.

As illustrated in FIG. 8, a high-speed cache 801 can be connected to, or incorporated in, the processor 802 to provide a high-speed memory for instructions or data that have been recently, or are frequently, used by processor 802. The processor 802 is connected to a north bridge 806 by a processor bus 805. The north bridge 806 is connected to random access memory (RAM) 803 by a memory bus 804 and manages access to the RAM 803 by the processor 802. The north bridge 806 is also connected to a south bridge 808 by a chipset bus 807. The south bridge 808 is, in turn, connected to a peripheral bus 809. The peripheral bus can be, for example, PCI, PCI-X, PCI Express, or other peripheral bus. The north bridge 806 and south bridge 808 are often referred to as a processor chipset and together manage data transfer between the processor 802, RAM 803, and peripheral components on the peripheral bus 809. In some architectures, the functionality of the north bridge can be incorporated into the processor instead of using a separate north bridge chip. In some embodiments, system 800 can include an accelerator card 812 attached to the peripheral bus 809. The accelerator card 812 can include field programmable gate arrays (FPGAs) or other hardware for accelerating certain processing.

Software Interface(s).

Software and data are stored in external storage 813 and can be loaded into RAM 803 and/or cache 801 for use by the processor 802. The system 800 includes an operating system for managing system resources. Non-limiting examples of operating systems include: Linux, Windows®, macOS®, BlackBerry OS®, iOS®, Android and other functionally-equivalent operating systems, as well as application software running on top of the operating system. In this example, system 800 also includes network interface cards (NICs) 810 and 811 connected to the peripheral bus for providing network interfaces to external storage, such as Network Attached Storage (NAS) and other computer systems that can be used for distributed parallel processing.

Computer Systems.

Figure 9:
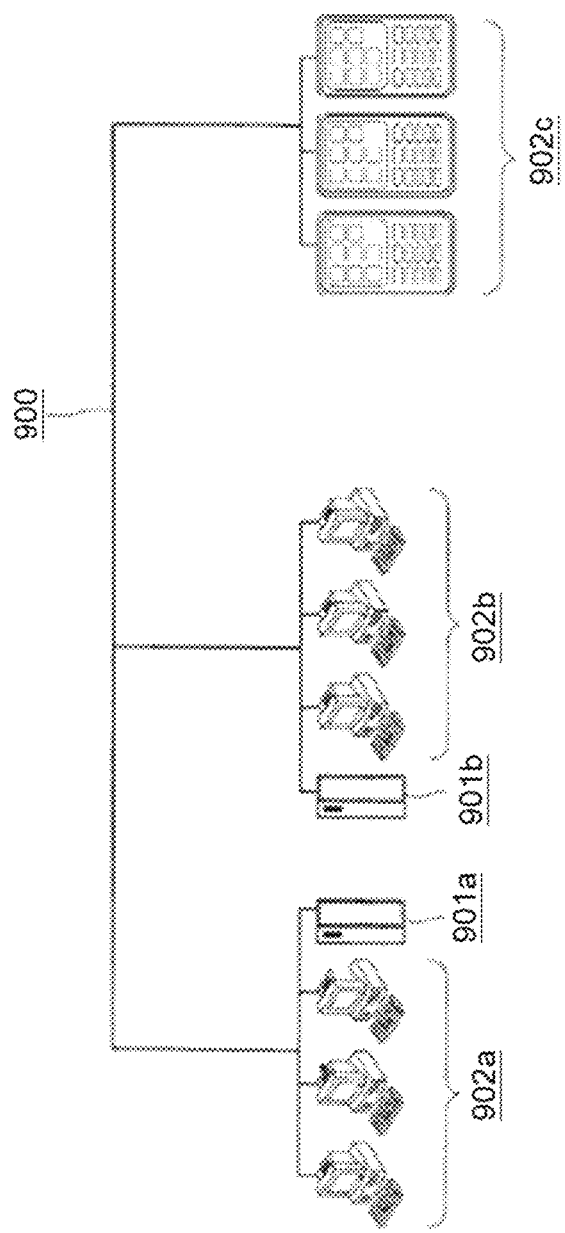
FIG. 9 is a diagram illustrating a computer network that can be used in connection with example embodiments of the invention.

FIG. 9 is a diagram showing a network 900 with a plurality of computer systems 902a, and 902b, a plurality of cell phones and personal data assistants 902c, and Network Attached Storage (NAS) 901a and 901b. In some embodiments, systems 902a, 902b, and 902c can manage data storage and optimize data access for data stored in NAS 901a and 902b. A mathematical model can be used for the data and be evaluated using distributed parallel processing across computer systems 902a and 902b, and cell phone and personal data assistant systems 902c. Computer systems 902a and 902b, and cell phone and personal data assistant systems 902c can also provide parallel processing for adaptive data restructuring of the data stored in NAS 901a and 901b. FIG. 9 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as NAS through a separate network interface.

In some embodiments, processors can maintain separate memory spaces and transmit data through network interfaces, back plane, or other connectors for parallel processing by other processors. In some embodiments, some or all of the processors can use a shared virtual address memory space.

Virtual Systems.

Figure 10:
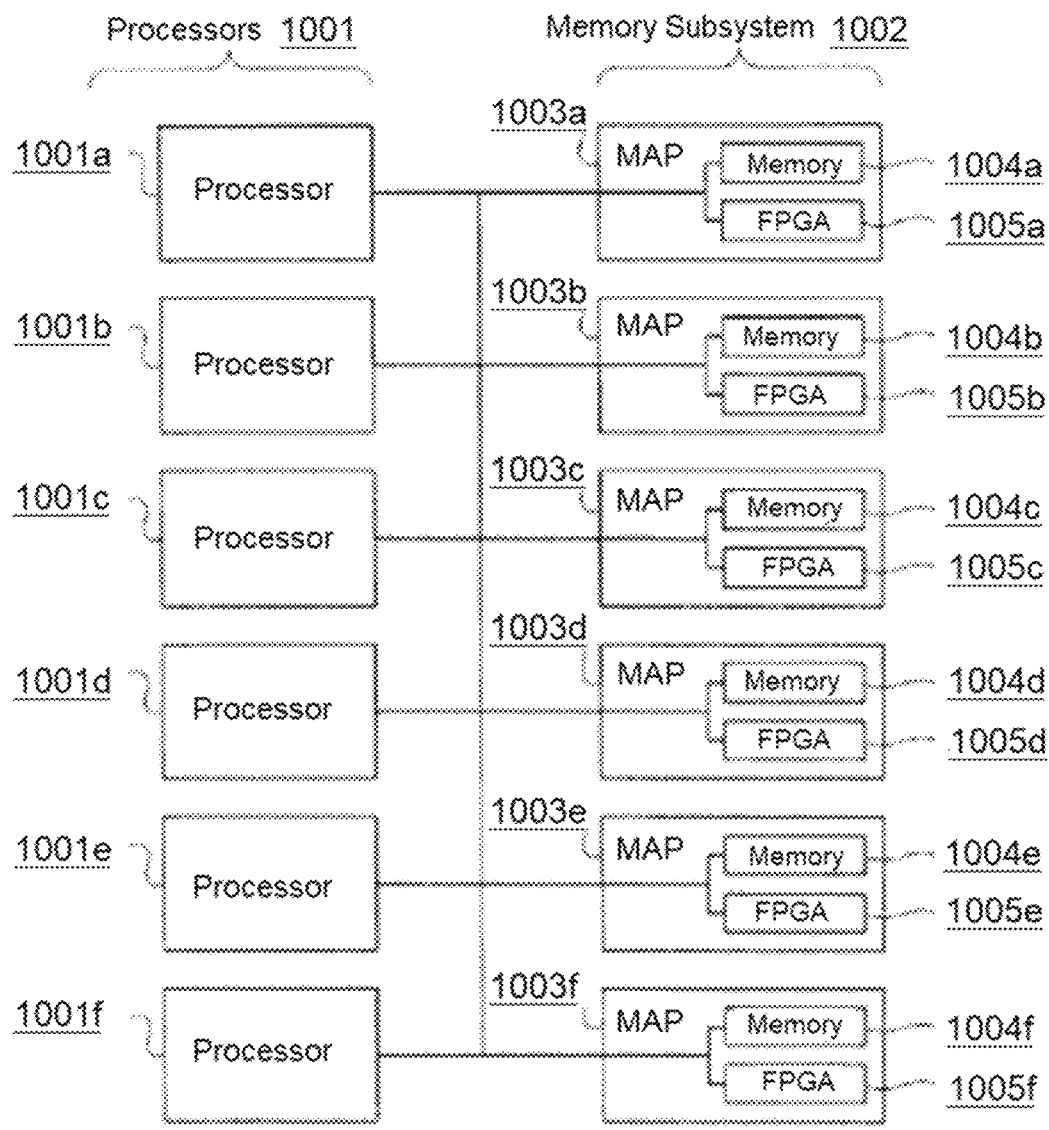
FIG. 10 is a diagram illustrating a second example architecture of a computer system that can be used in connection with example embodiments of the invention.

FIG. 10 is a diagram of a multiprocessor computer system using a shared virtual address memory space. The system includes a plurality of processors 1001, i.e., 1001a-f, that can access a shared memory subsystem 1002. The system incorporates a plurality of programmable hardware memory algorithm processors (MAPs) 1003a-f in the memory subsystem 1002. Each MAP 1003a-f can comprise a memory 1004a-f and one or more field programmable gate arrays (FPGAs) 1005a-f. The MAP provides a configurable functional unit and particular algorithms, or portions of algorithms, can be provided to the FPGAs 1005a-f for processing in close coordination with a respective processor. In this example, each MAP is globally accessible by all of the processors for these purposes. In one configuration, each MAP can use Direct Memory Access (DMA) to access an associated memory 1004a-f, thereby allowing the MAP to execute tasks independently of, and asynchronously from, the respective microprocessor 1001a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 10, system on chips (SOCs), application specific integrated circuits (ASICs), or other processing and logic elements. For example, the Set Processor and Optimizer can be implemented with hardware acceleration through the use of a hardware accelerator card, such as accelerator card 812 illustrated in FIG. 8.

Figure 11:
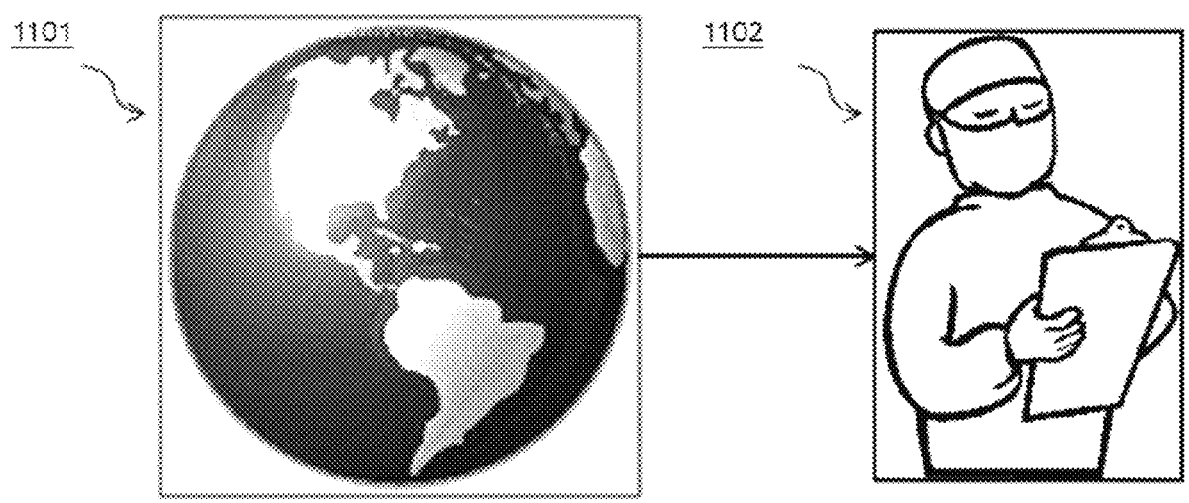
FIG. 11 illustrates a global network that can transmit a product of the invention.

Any embodiment of the invention described herein can be, for example, produced and transmitted by a user within the same geographical location. A product of the invention can be, for example, produced and/or transmitted from a geographic location in one country and a user can be present in a different country. In some embodiments, the data accessed by a system described herein is a computer program product that can be transmitted from one of a plurality of geographic locations 1101 to a user 1102 (FIG. 11). Data generated by a computer program product described herein can be transmitted back and forth among a plurality of geographic locations, for example, by a network, a secure network, an insecure network, an internet, or an intranet. In some embodiments, an ontological hierarchy can be encoded on a physical and tangible product.

Any embodiment of the invention described herein can be produced and/or transmitted in an encoded form, for example, a radio frequency identification tag or barcode. In some embodiments, the data accessed by a system described herein can be accessed from the encoded form either directly or as part of a health record. In some embodiments, the health record can be an electronic health record or digital health record. In some embodiments, the health record can be accessed by the subject or a health care provider for the subject.

Example 4. ECG Validation Measurements

Figure 14:
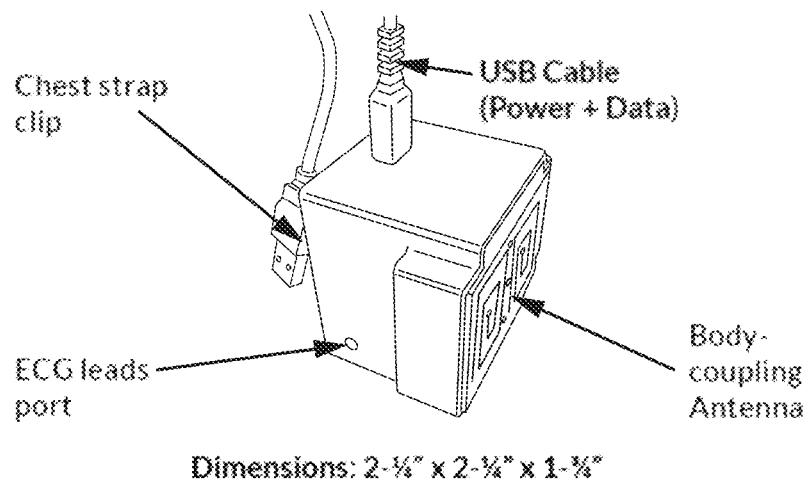
FIG. 14 depicts a representative system of the invention.
Figure 15:
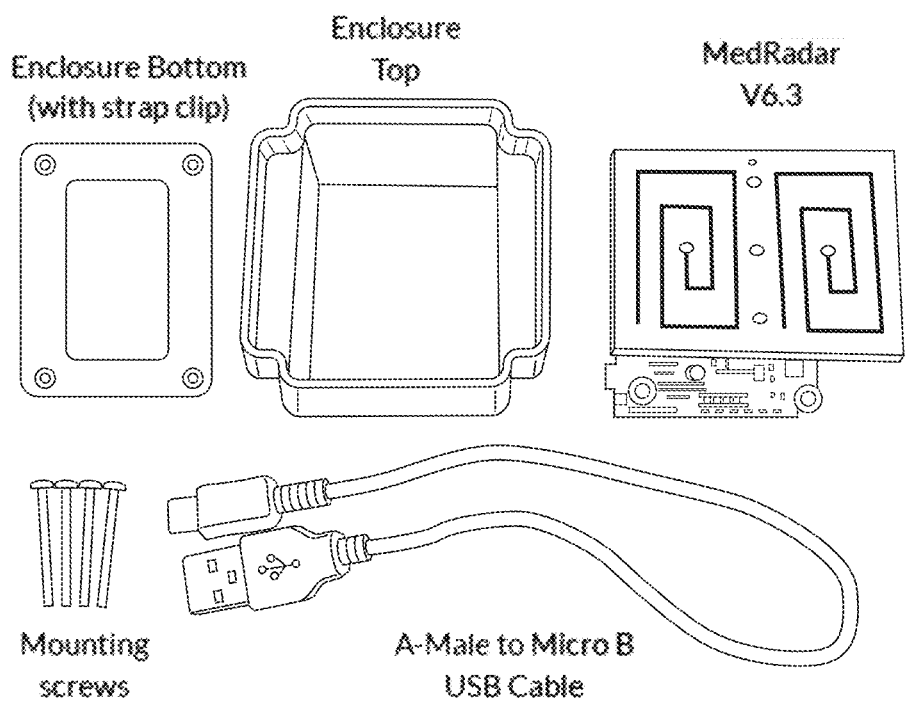
FIG. 15 depicts components of the example device of the invention.
Figure 16:
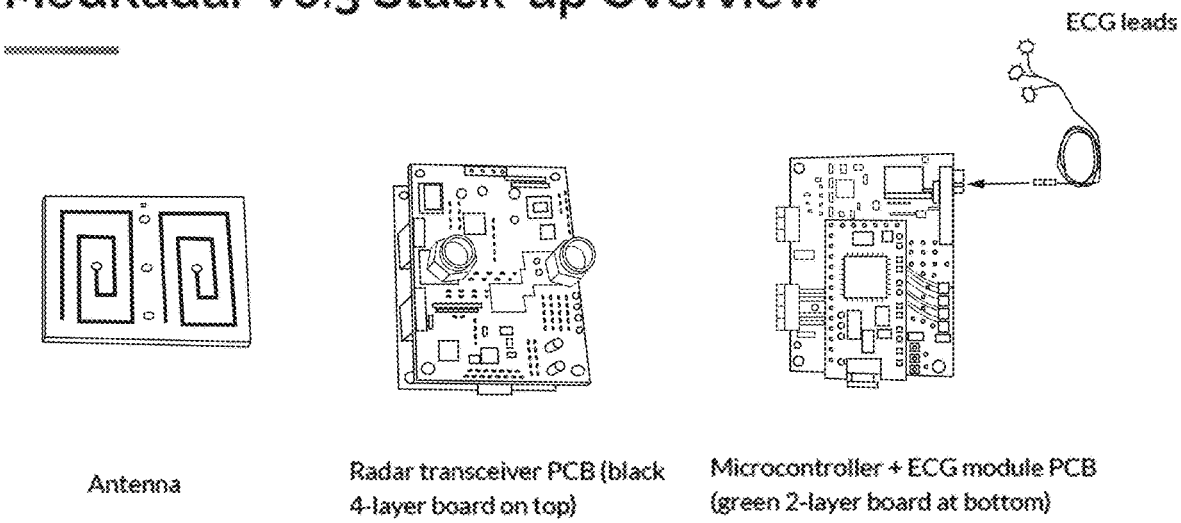
FIG. 16 depicts components of the transceiver of the device of the invention.

FIG. 14 depicts an example device of the invention. The device contains a chest strap clip, a USB cable, a body-coupling antenna, and an ECG leads port. FIG. 15 depicts components of the example device of the invention. The housing of the device is comprised of an enclosure bottom with a strap clip and an enclosure top. The device also contains a transceiver (MedRadar® V6.3), mounting screws, and a A-Male to Micro B USB cable. FIG. 16 depicts components of the transceiver, which comprises two directional antennas (one for transmitting signals and the other for receiving signals), a radar transceiver PCB (4-layer circuit board on top), and a microcontroller with ECG module PCB (2-layer circuit board on the bottom). The device further comprises 3 ECG leads that connect to an ECG port of the ECG module PCB.

Figure 17:
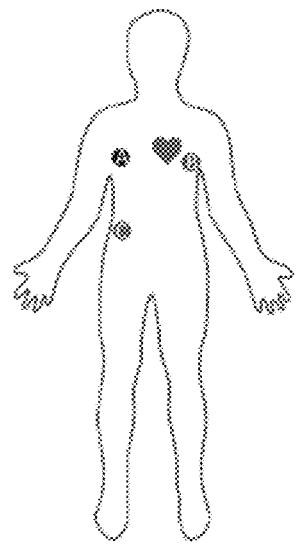
FIG. 17 illustrates an example placement of ECG electrode leads on a human subject.
Figure 18:
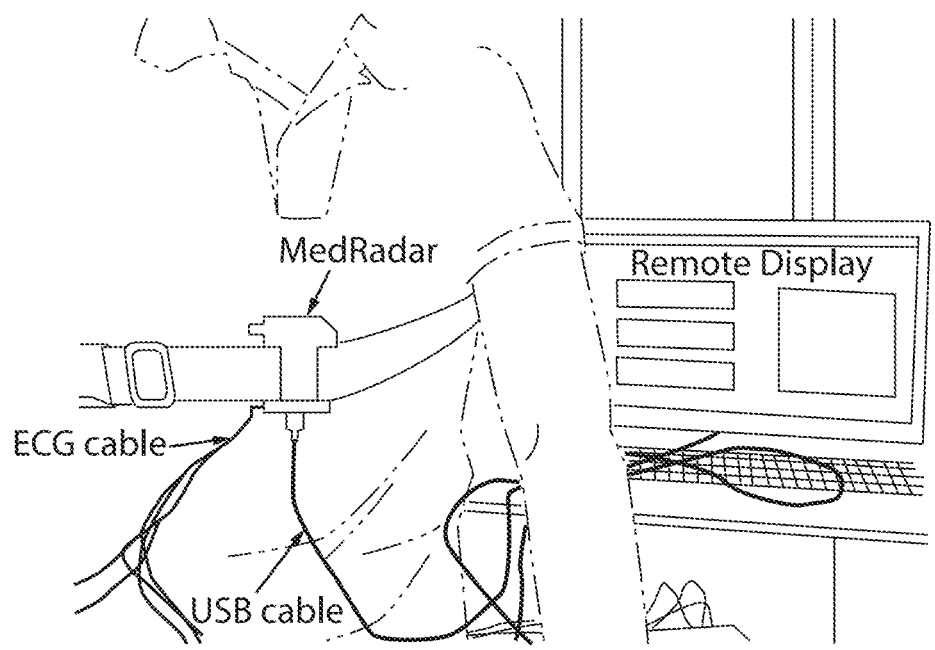
FIG. 18 illustrates an example placement of an example device of the invention on a human subject.
Figure 19:
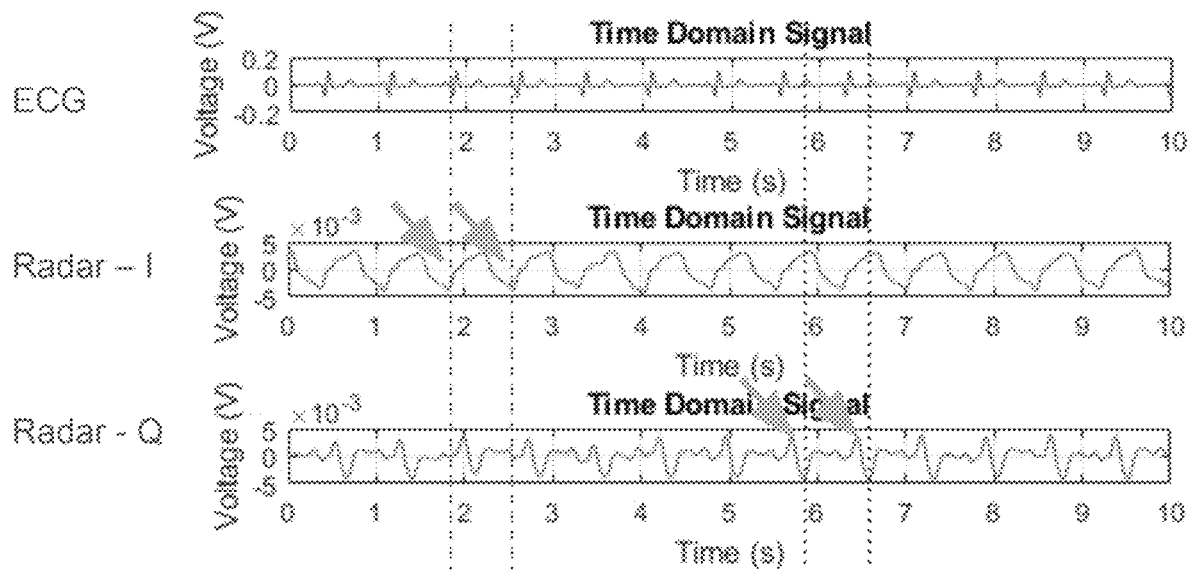
FIG. 19 illustrates paired ECGs and FQ radar measurements with an example device of the invention on a human subject.
Figure 20:
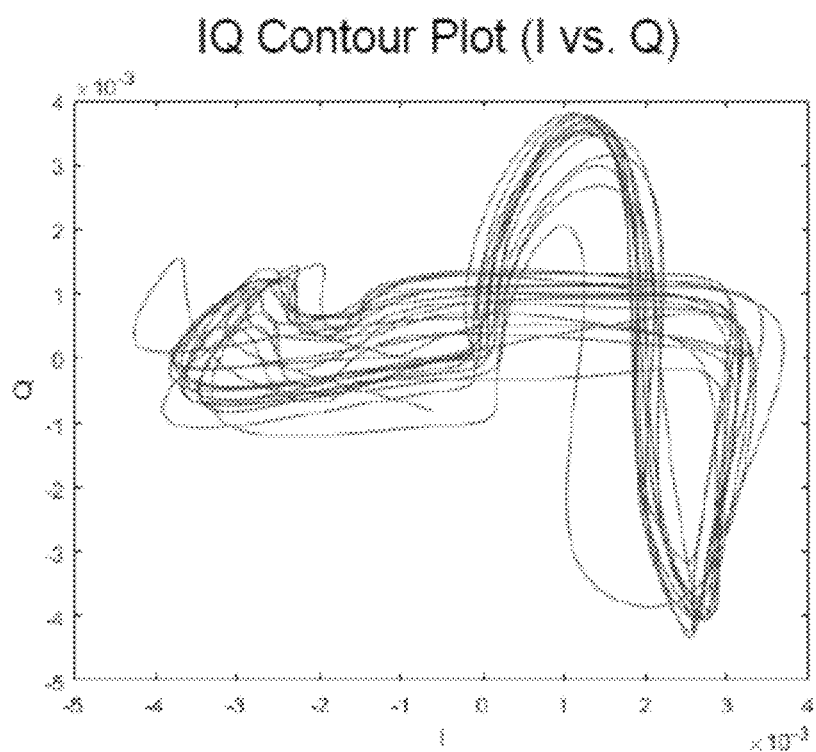
FIG. 20 illustrates an FQ contour plot of the detected FQ radar measurements.

To validate methods described herein, signal measurements using quadrature Doppler radar and standard ECG were obtained using the example device. ECG measurements were obtained by 3 lead electrodes placed to the torso of the subject (i.e., in proximity to the right arm, left arm, and right leg) as illustrated in FIG. 17. The device was placed to the sternum of a human subject, in direct contact with the subject, and fastened by a chest strap (FIG. 18). Synchronized ECGs and I/Q measurements obtained from the device are shown in FIG. 19. Correlations between the ECGs and I/Q signals are indicated by the arrows. The dashed lines highlight a correlation between the valleys in the I signal with the end of the P-wave in the ECG. The dotted lines highlight a correlation between the valleys in the Q signal with the T-wave peak in the ECG. FIG. 20 illustrates a two-dimensional I/Q contour plot of the detected I/Q radar measurements.

Example 5. Ultrasonography (Echocardiogram) Validation Measurements

Figure 21:
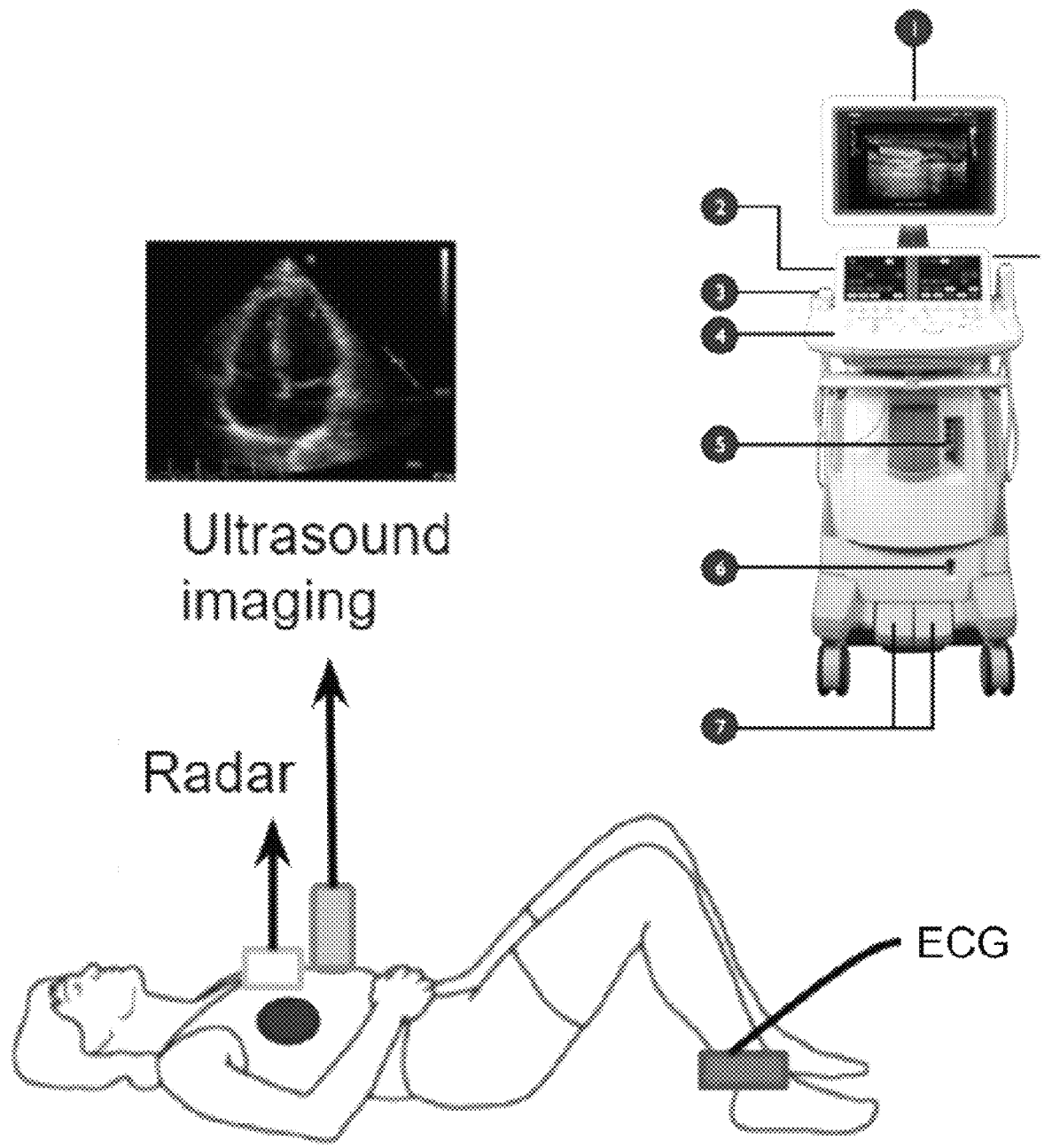
FIG. 21 illustrates an example setup of a transthoracic ultrasound validation experiment.

FIG. 21 illustrates an example setup of a validation experiment for the device described herein using ultrasound. The radar device was placed to the sternum of a human subject and in contact with the subject. An ultrasound transducer was placed to the apex between the ribs in proximity to the heart of the subject. Synchronized measurements were obtained from an echocardiogram machine (Siemens®) and a custom-made ECG module placed to the right ankle of the subject.

Figure 22:
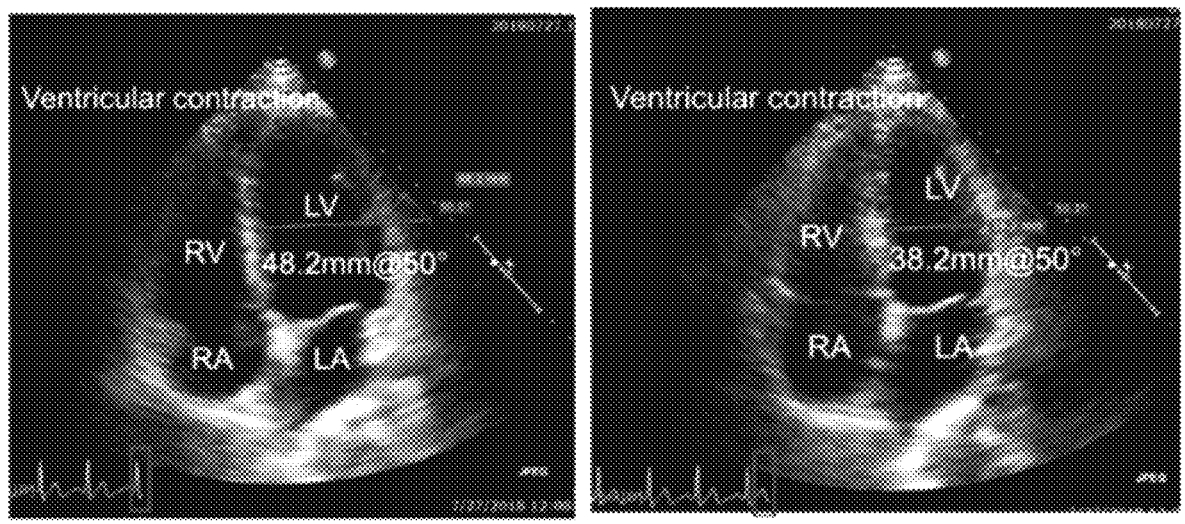
FIG. 22 illustrates ultrasound images generated from the ultrasound validation experiment.

As illustrated in FIG. 22, the end of T-wave (left) marked the maximum left ventricular contraction. The end of the contraction period (right) marked the maximum distance between the radar and the heart wall covering the left ventricle. Total contraction length of the left ventricle was estimated to be about 10 mm (from 48.2 mm to 38.2 mm). Thus, the radar signal is sensitive to relatively small movements of the heart (on the order of millimeters). The peak of the T-wave can be correlated to a midpoint of contraction, e.g., maximum speed or transition point between acceleration and deceleration, that yields valleys in the radar measurements as shown in FIG. 19.

Example 6. Validation Measurements Using the Valsalva Maneuver

A further validation experiment for the device described herein was conducted by performance of the Valsalva maneuver. The experiment was verified by ultrasound. The Valsalva maneuver is medical diagnostic in which a subject forcefully exhales against a closed airway. The closed airway is produced by closing the mouth and pinching the nose shut while exhaling as if blowing up a balloon. This procedure causes changes in intrathoracic pressure that dramatically affects venous return, cardiac output, arterial pressure, and heart rate. The reduced venous return limits normal filling and expansion of the cardiac chambers, in particular, the RV. A size reduction in heart chamber volume essentially increases the nominal distance between the surface of the chest and the heart wall, as well as deforming the shape of the heart.

Figure 23:
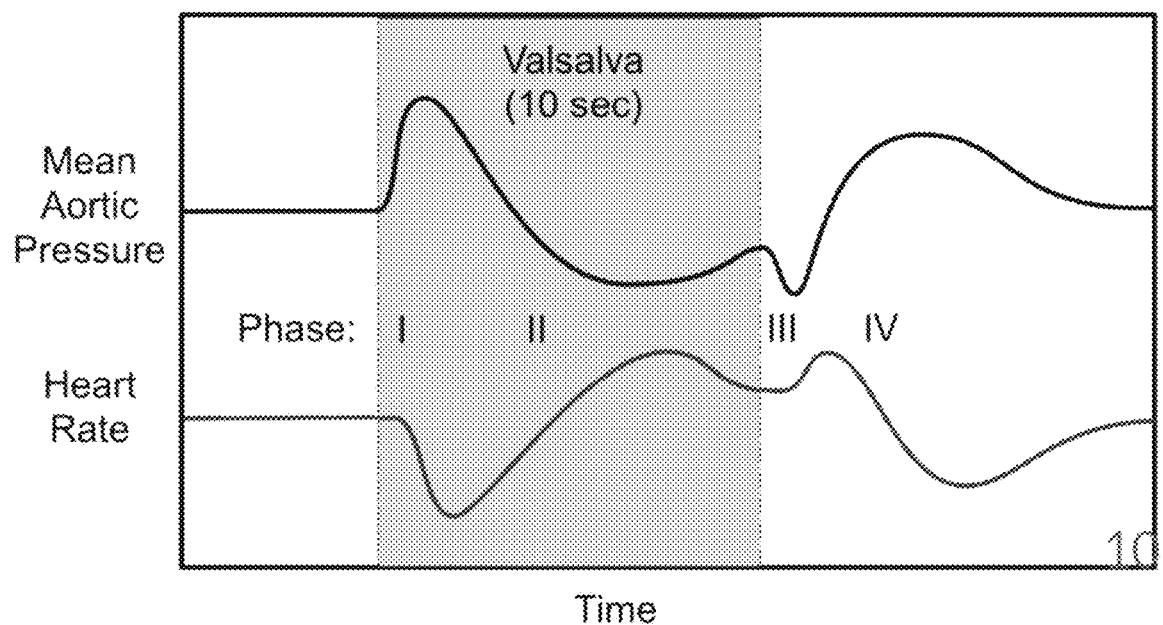
FIG. 23 illustrates the mechanism of the Valsalva maneuver.

As illustrated in FIG. 23, the physiological response to the Valsalva maneuver consists of four phases: I) initial pressure rise, II) reduced venous return and compensation, III) pressure release, and IV) return of cardiac output. At phase I, the application of expiratory force causes pressure to rise inside the chest forcing blood out of the pulmonary circulation into the left atrium. This force causes a mild rise in stroke volume during the first few seconds of the maneuver. At phase II, return of systemic blood to the heart is impeded by elevated chest pressure. The cardiac output of the heart is then reduced and stroke volume falls. The fall in stroke volume reflexively causes blood vessels to constrict with a slight rise in pressure for about 15-20 seconds. This compensation can be quite significant with pressure returning to near or even above normal, while the cardiac output and blood flow to the body remain low. During this time, the heart rate increases (compensatory tachycardia). At phase III, the chest pressure is released, allowing the pulmonary vessels and the aorta to re-expand causing a further initial slight fall in stroke volume due to decreased left atrial return and increased aortic volume. Venous blood can then re-enter the chest and heart, and cardiac output begins to increase. At phase IV, return of blood to the heart is enhanced by the effect of entry of blood, which had been dammed back, causing a rapid increase in mean aortic pressure. The stroke volume usually rises above normal before returning to a normal level. With return of blood pressure, the pulse rate then gradually normalizes.

Figure 24:
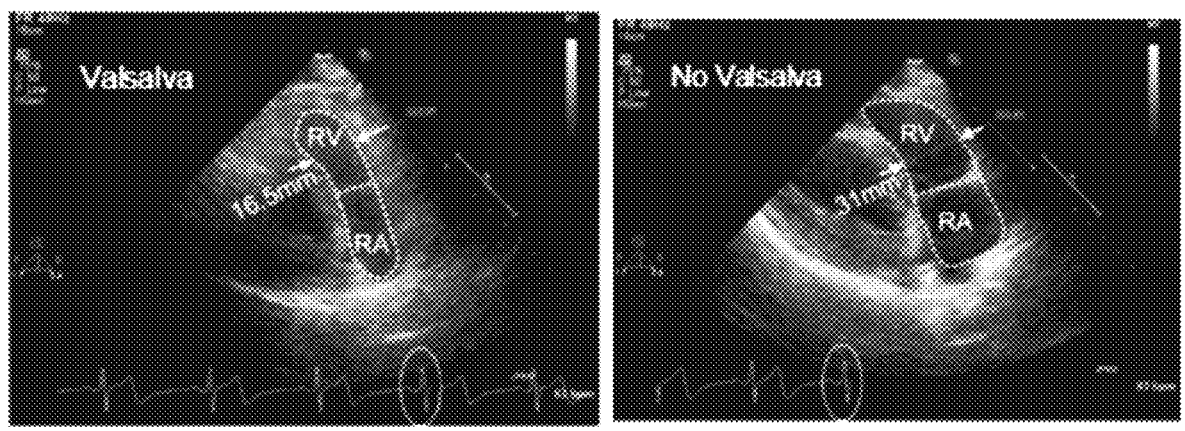
FIG. 24 illustrates ultrasound images generated during performance of the Valsalva maneuver and without the maneuver.

FIG. 24 illustrates sonograms generated during performance of the Valsalva maneuver (left panel) versus no performance of the Valsalva maneuver (right panel). The Valsalva maneuver caused decreased filling of the right chambers (right ventricle, RV; and right atrium, RA). Thus, the Valsalva maneuver can be used to mimic changes to the volume, size, or shape of the chambers of the heart, for example, in cases of changes in PA pressure.

Figure 25:
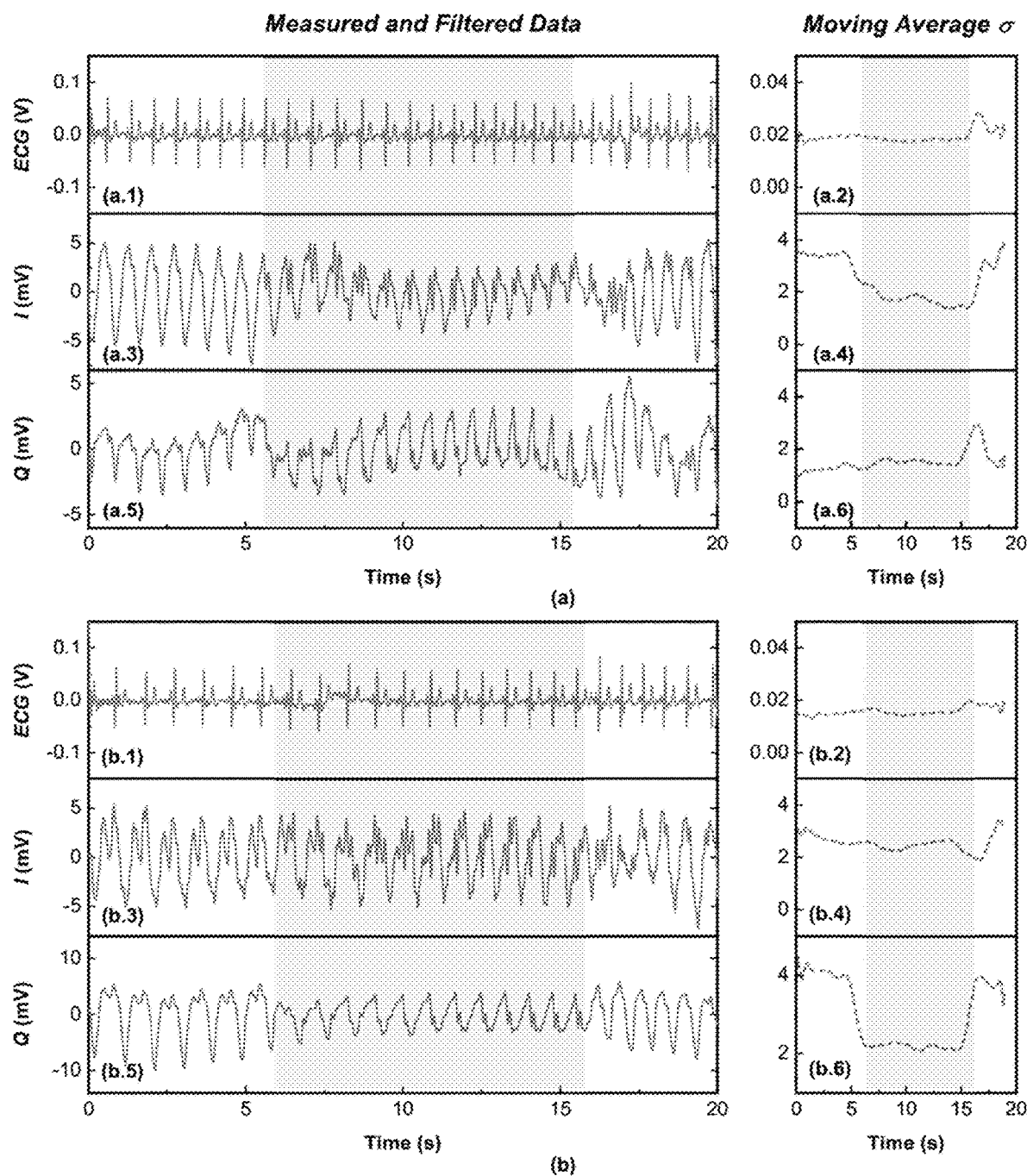
FIG. 25 illustrates paired ECGs and FQ radar measurements during performance of the Valsalva maneuver.

FIG. 25 illustrates synchronized ECGs and quadrature Doppler radar measurements obtained during performance of the Valsalva maneuver (gray shading). During performance of the Valsalva maneuver, the volume of the RV decreases. There is a clear distinction in I/Q radar signal amplitude and shape between the Valsalva region and those before and after. The moving average standard deviation associated to each I/Q signal shows the characteristic changes within the Valsalva region. Since ECG measures the electrical signals of the heart, spatial changes of the heart due to the Valsalva maneuver were not observable. Thus, quadrature radar signal variations can be used to determine physical size changes of the RV and the LV.

Example 7. Validation Measurements Using a Pig with Elevated PA Pressure

Figure 26:
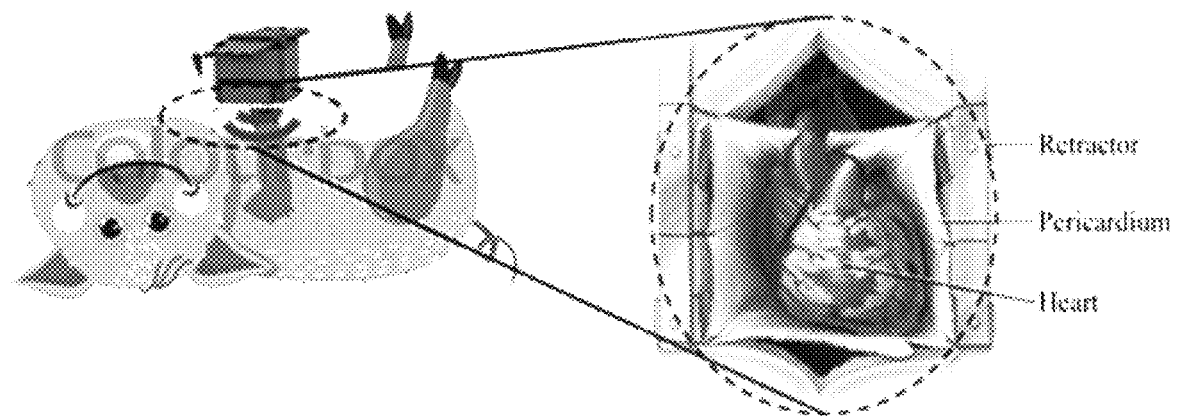
FIG. 26 illustrates placement of radar sensor inside an opened chest of an anesthetized pig.
Figure 27:
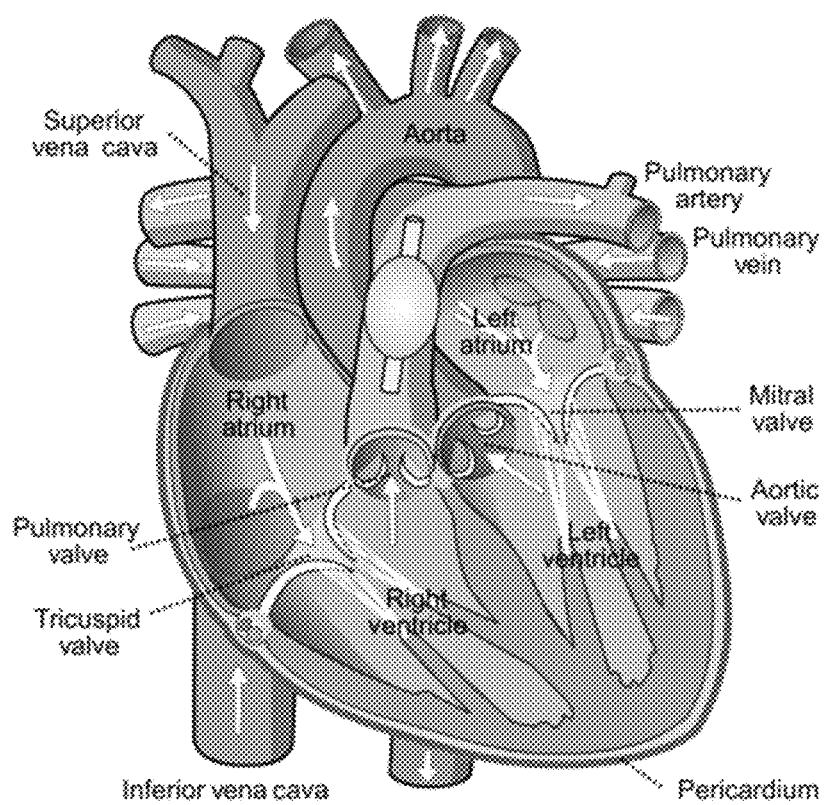
FIG. 27 illustrates a technique of monitoring PA pressure changes using a pig subject in which right ventricle (RV) pressure was increased using balloon occlusion in the pulmonary artery of the pig heart.
Figure 28:
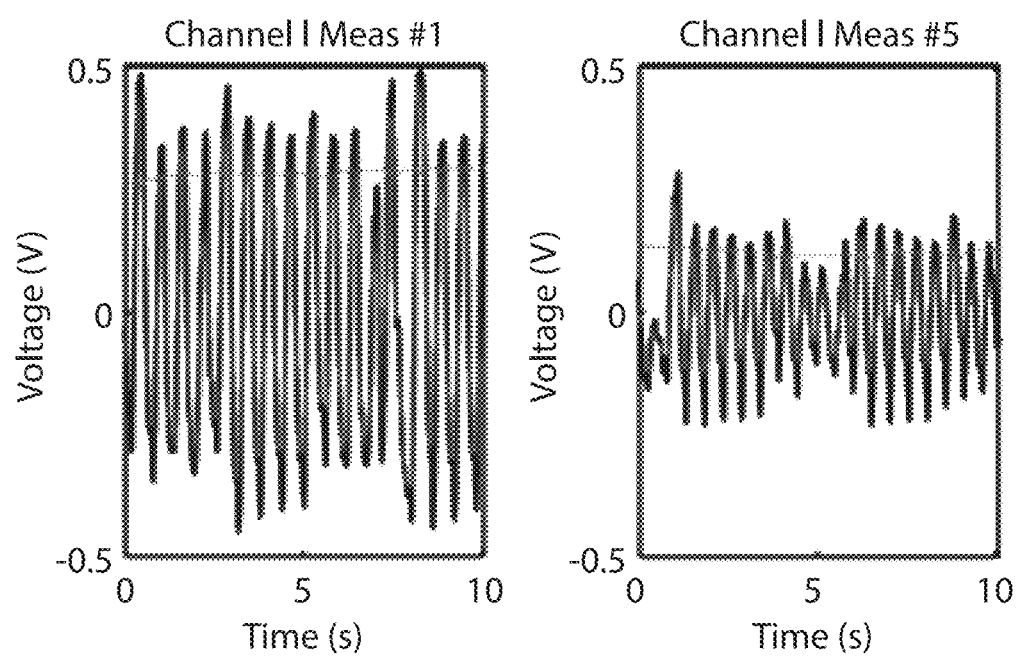
FIG. 28 illustrates FQ radar measurements of RV motion due to manual increase of PA pressure in a pig model.
Figure 29:
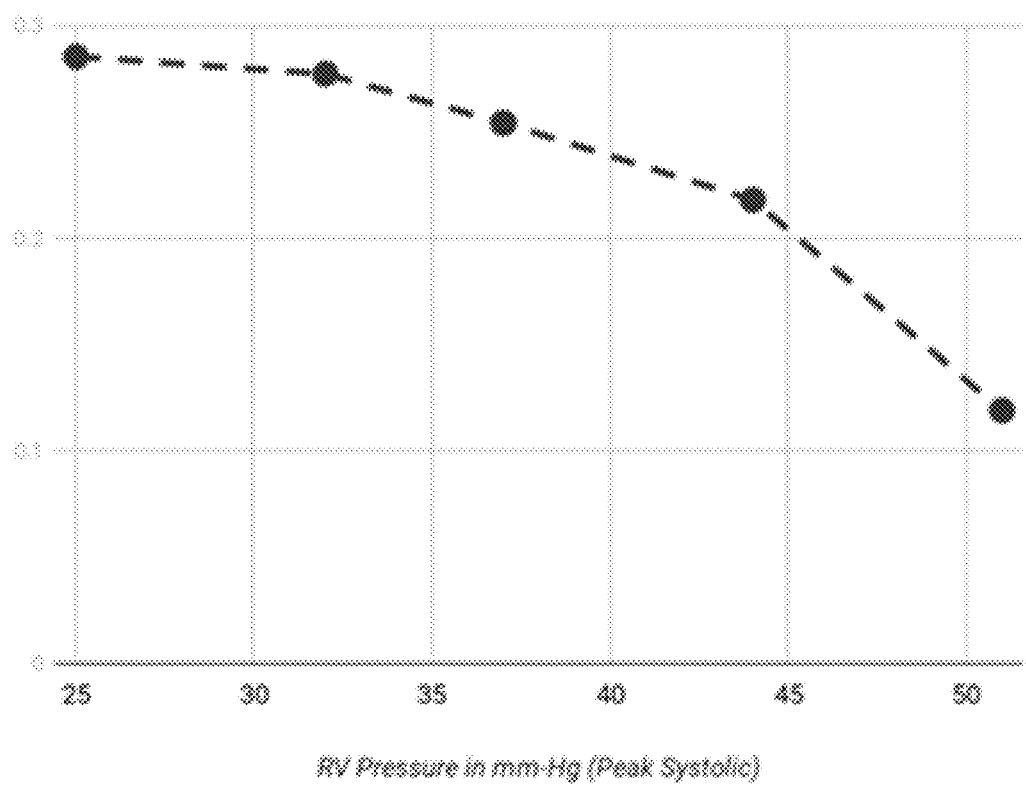
FIG. 29 illustrates a plot of time-averaged standard deviation amplitude for the I channel signal as a function of RV pressure.

Direct monitoring of RV motion with quadrature Doppler radar was validated in an anesthetized pig while adjusting the PA pressure. An example device of the invention was placed inside the opened chest of the animal with line-of-sight to the animal's beating heart (FIG. 26). The device was fastened to the edge of the opening, leaving an air gap between the antenna of the device and the heart wall. During measurement, the RV pressure in the heart was increased by implantation of a balloon inside the PA to progressively increase PA pressure (FIG. 27). The resulting Doppler radar I/Q channel measurements are shown in FIG. 28. From measurement #1 to #5 (Channel-I Meas #1 and Channel-I Meas #5), the systolic pressure increased from 25 mmHg to 51 mmHg. Elevated RV pressure caused enlargement of the RV and reduction of the expansion/contraction capability of the animal's heart. As shown in FIG. 28, the overall (average) peak-to-peak amplitudes of the raw signal oscillations for the I channel (denoted by the white lines) diminished as a result of increasing PA pressure. An averaged moving standard deviation (STD) value was used to quantify the relative amplitude changes. The time-averaged standard deviation of the amplitude for the I channel signal as a function of RV pressure was plotted in FIG. 29. The plot shows a non-linear relationship between signal amplitude and RV pressure. As RV pressure (or PA pressure) increased, signal amplitude of RV motion decreased.

Example 8. Device Reproducibility and Motion Detection Resolution

Figure 30:
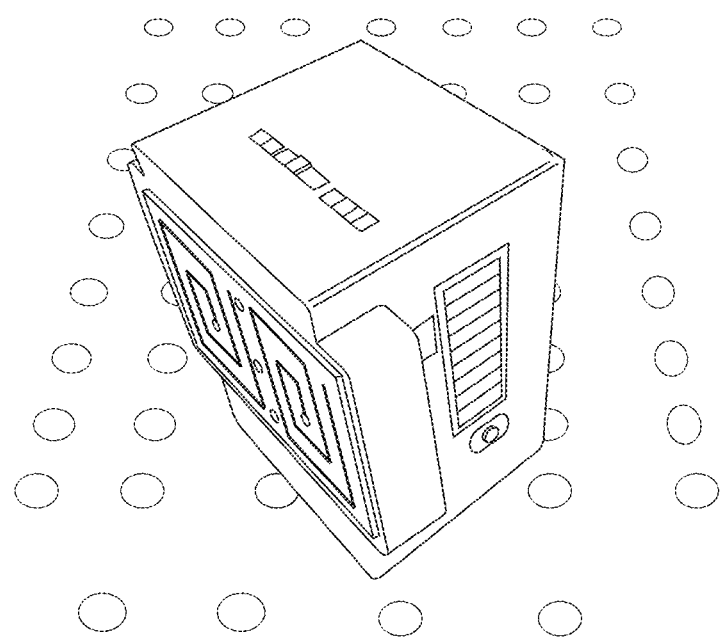
FIG. 30 depicts a representative system of the invention.
Figure 31:
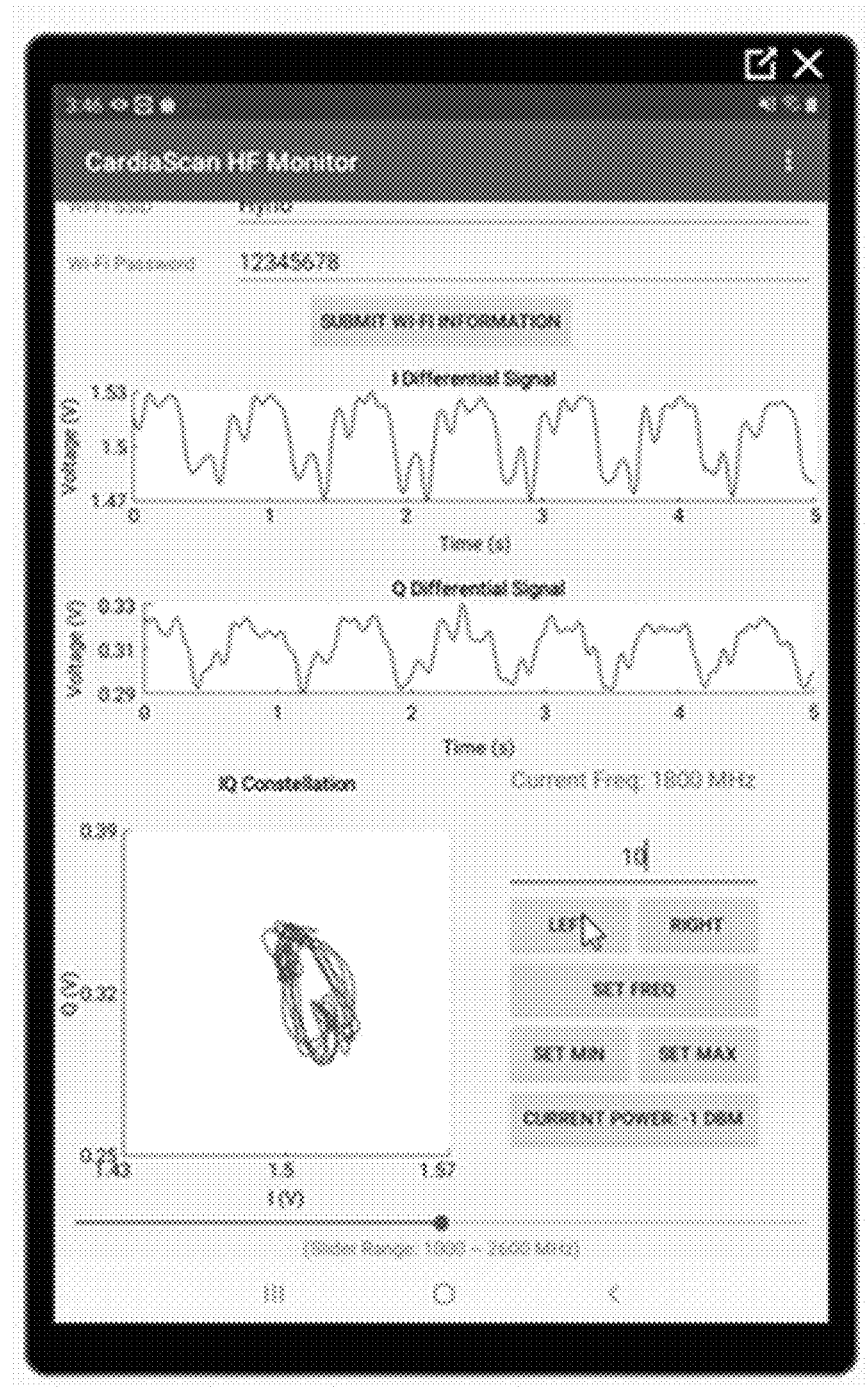
FIG. 31 depicts a representative remote display platform.

FIG. 30 depicts a representative wireless system of the invention. The device contains a Wi-Fi/BLE enabled microcontroller configured for wireless data transfer and operations. FIG. 31 depicts a representative remote display platform of a software application communicatively coupled to the system. The application can display real-time data acquired by the device, display time domain data, adjust radio frequency and power of the device when needed.

To validate stability of the device over an extended period of time, a pair of linear actuators were used to mimic cardiac motions, each representing right ventricle motion (motion #1) and right atrium motion (motion #2), respectively. Each actuator carried a metal plate; the motion of the plates represents heart wall motions on the order of millimeters. The device was placed at a distance from the plates to measure dual motions of the plates at a close range.

Figure 32:
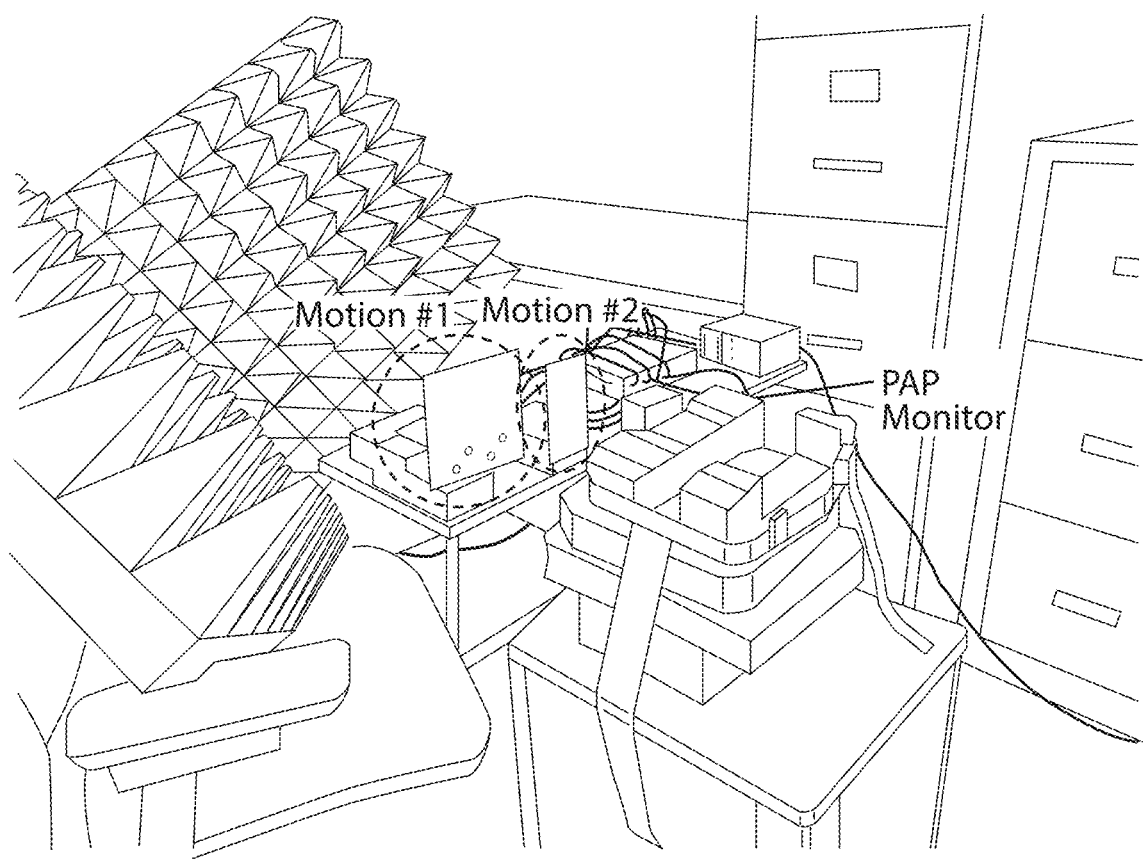
FIG. 32 depicts a representative system of the invention.
Figure 33:
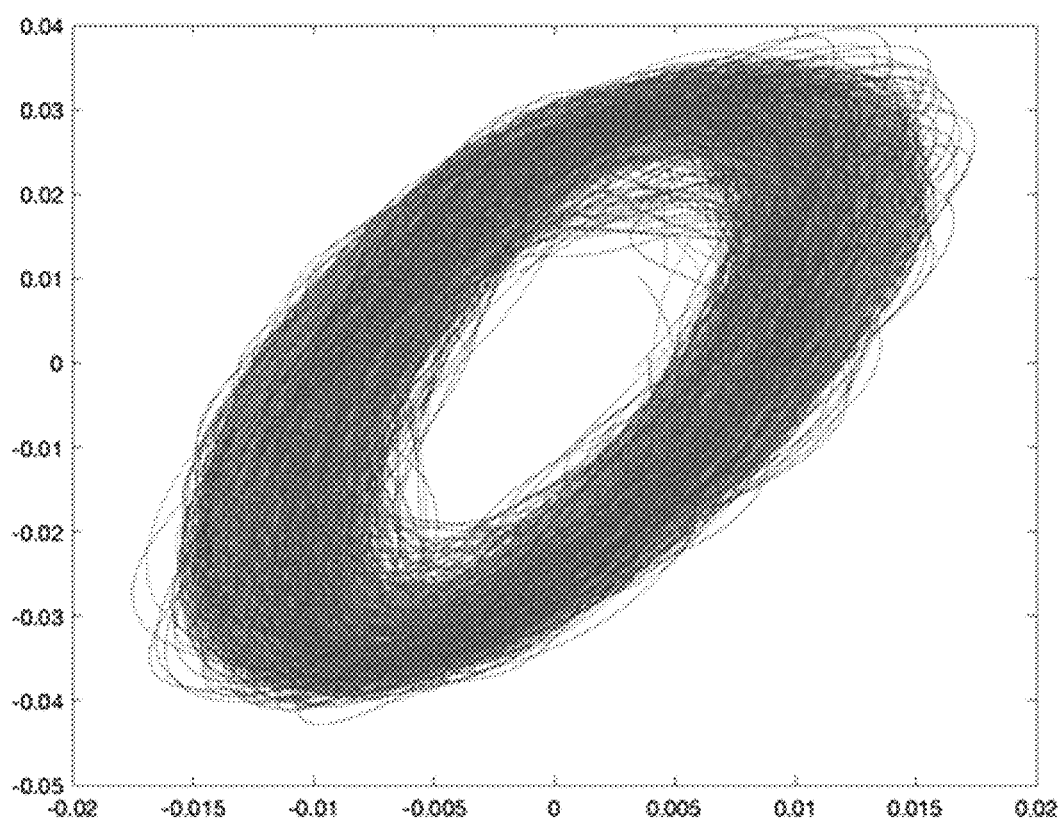
FIG. 33 depicts the radar output data from multi-day testing.

The validation tests began on day 1 with linear actuators performing sinusoidal motions with a peak-to-peak amplitude of 10 millimeters and 5 millimeters, respectively, and at the same oscillation frequency of 1 Hz. Throughout 4 days of tests, 40 datasets were acquired. The tests were performed in a controlled room where no objects were relocated during the multi-day tests. FIG. 32 shows the validation test setup. FIG. 33 illustrates the 40 sets of radar outputs overlapped in one plot. Quantitative analysis of the output data showed a multiday variance of less than 4%.

Figure 34:
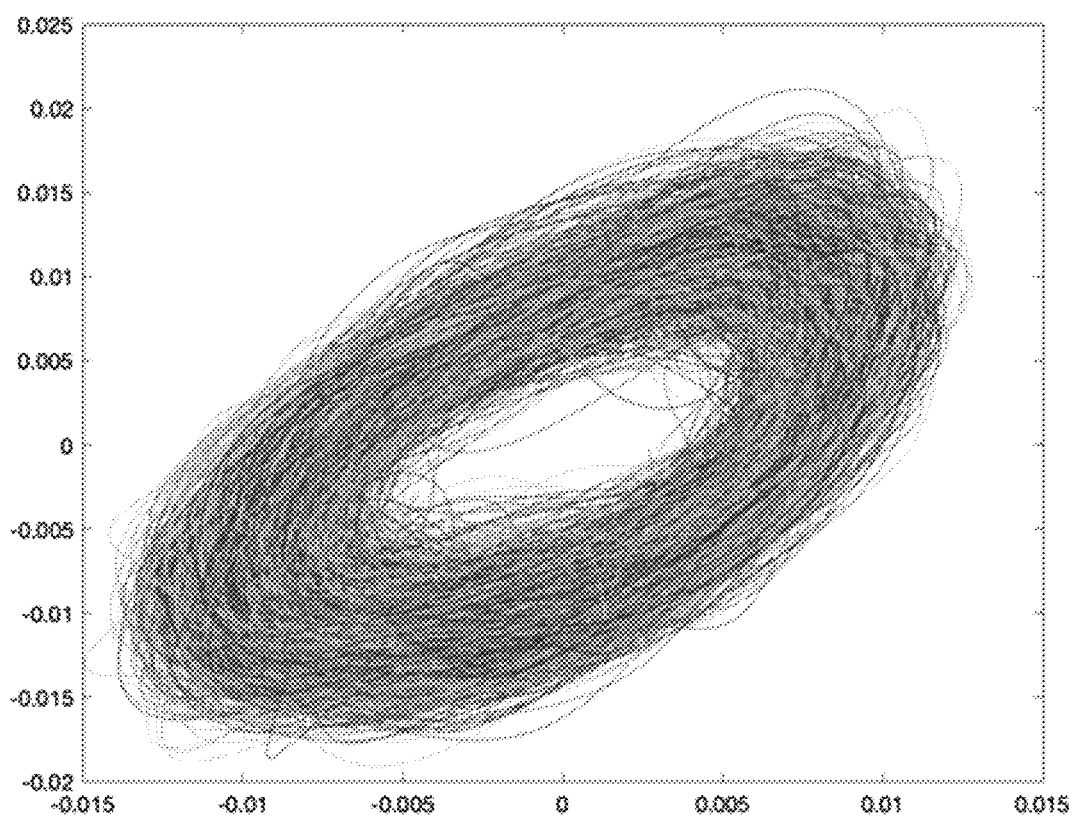
FIG. 34 depicts the radar output data from resolution testing.
Figure 35:
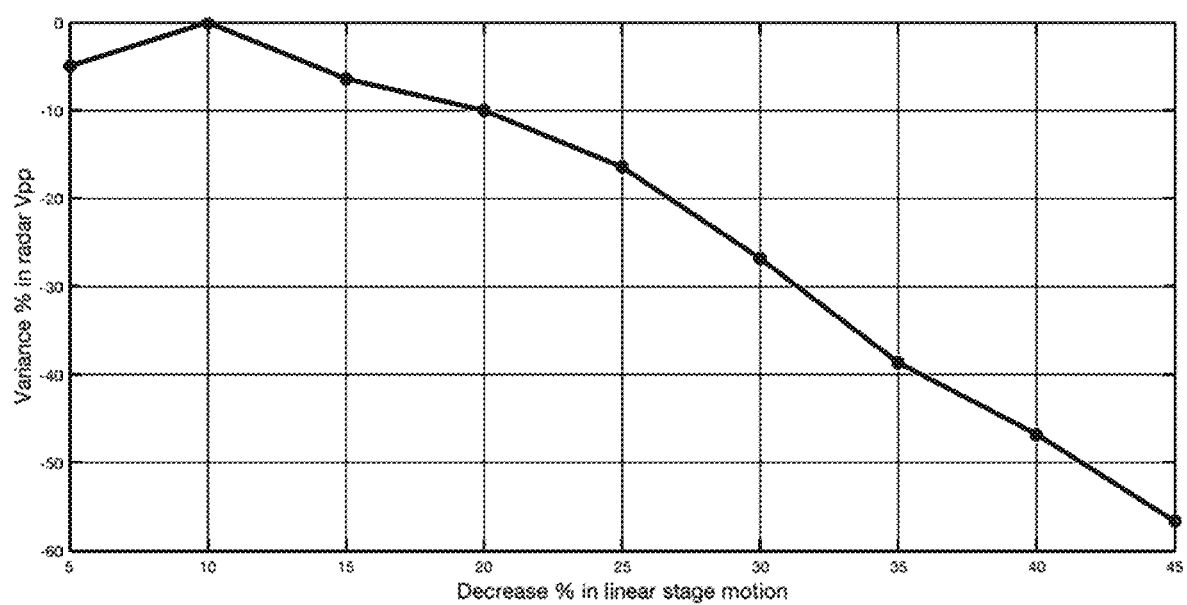
FIG. 35 depicts the variance of the radar output data from resolution testing.

To identify changes in wall motion as a result of varying PAPP, the resolution of motion detection by the device was tested. In a similar setup as FIG. 32, two linear actuators carrying metal plates were programmed to perform a series of sinusoidal motions with decreasing amplitudes. Phantom #1 outputted motions from 10 millimeters to 5.5 millimeters, whereas phantom #2 outputted motions from 5 millimeters and 2.75 millimeters, both in a 5% decline rate. FIG. 34 depicts the resulting radar output data. Quantitative analysis of the output data showed approximately a 4.5% decrease as shown in FIG. 35. The resulting data verify that the radar outputs track the change in target motion depth.

EMBODIMENTS

The following non-limiting embodiments provide illustrative examples of the invention, but do not limit the scope of the invention.

Embodiment 1. A method for monitoring a change in pulmonary artery pressure in a subject, the method comprising: a) transmitting by a transmitter of a transceiver device a wavelength of an electromagnetic radiation to a heart of the subject; b) detecting by a receiver of the transceiver device using Doppler radar sensing an electromagnetic signal reflected off the heart of the subject in response to the wavelength of the electromagnetic radiation; and c) determining by a processor based on the electromagnetic signal reflected off the heart of the subject the change in pulmonary artery pressure in the subject.

Embodiment 2. The method of Embodiment 1, wherein the determining of the change in pulmonary artery pressure in the subject is determined by an analysis of a movement of a portion of the heart.

Embodiment 3. The method of Embodiment 1, wherein the determining of the change in pulmonary artery pressure in the subject is determined by an analysis of a movement of a chamber of the heart.

Embodiment 4. The method of Embodiment 2 or 3, wherein the movement is an expansion of a chamber of the heart.

Embodiment 5. The method of Embodiment 2 or 3, wherein the movement is a contraction of a chamber of the heart.

Embodiment 6. The method of Embodiment 1, wherein the determining of the change in pulmonary artery pressure in the subject is determined by an analysis of a volume change of a chamber of the heart.

Embodiment 7. The method of any one of Embodiments 3-6, wherein the chamber of the heart is a right ventricle.

Embodiment 8. The method of any one of Embodiments 3-6, wherein the chamber of the heart is a left ventricle.

Embodiment 9. The method of any one of Embodiments 3-6, wherein the chamber of the heart is a right atrium.

Embodiment 10. The method of any one of Embodiments 3-6, wherein the chamber of the heart is a left atrium.

Embodiment 11. The method of any one of Embodiments 1-10, wherein the determined change in pulmonary artery pressure in the subject is associated with congestive heart failure.

Embodiment 12. The method of any one of Embodiments 1-11, wherein the wavelength of electromagnetic radiation transmitted to the heart of the subject is a radio wave.

Embodiment 13. The method of any one of Embodiments 1-12, wherein the detecting by the receiver is using continuous wave Doppler radar sensing.

Embodiment 14. The method of any one of Embodiments 1-13, wherein the detecting by the receiver is using microwave Doppler radar sensing.

Embodiment 15. The method of any one of Embodiments 1-14, wherein the Doppler radar sensing has a frequency range of about 800 MHz to about 3 GHz.

Embodiment 16. The method of any one of Embodiments 1-15, wherein the electromagnetic signal reflected off the heart of the subject has a frequency that is below 3 GHz.

Embodiment 17. The method of any one of Embodiments 1-16, wherein the receiver is a quadrature radar receiver.

Embodiment 18. The method of any one of Embodiments 1-17, wherein the electromagnetic signal is reflected off a surface of the heart of the subject.

Embodiment 19. The method of any one of Embodiments 1-18, wherein the transceiver device, transmitter, and the receiver are in a common housing.

Embodiment 20. The method of any one of Embodiments 1-19, wherein the transceiver device further comprises a microcontroller, a power module, a battery, or any combination thereof.

Embodiment 21. The method of any one of Embodiments 1-20, further comprising placing the transceiver device to a chest of the subject.

Embodiment 22. The method of any one of Embodiments 1-21, further comprising placing the transceiver device to a sternum of the subject.

Embodiment 23. The method of any one of Embodiments 1-22, wherein the subject is human.

Embodiment 24. The method of any one of Embodiments 1-23, wherein the subject is undergoing an intervention for heart failure, the method further comprising determining based on the electromagnetic signal reflected off the heart of the subject whether the intervention for the heart failure has modulated the pulmonary artery pressure.

Embodiment 25. The method of any one of Embodiments 1-24, further comprising determining based on the electromagnetic signal reflected off the heart of the subject a cardiac output of the heart of the subject.

Embodiment 26. The method of any one of Embodiments 1-25, further comprising determining based on the electromagnetic signal reflected off the heart of the subject a cardiac rhythm of the heart of the subject.

Embodiment 27. The method of any one of Embodiments 1-26, further comprising determining based on the electromagnetic signal reflected off the heart of the subject a stroke volume of the heart of the subject.

Embodiment 28. The method of any one of Embodiments 1-27, further comprising determining based on the electromagnetic signal reflected off the heart of the subject an ejection fraction of the heart of the subject.

Embodiment 29. The method of any one of Embodiments 1-28, further comprising determining based on the electromagnetic signal reflected off the heart of the subject a heart rate variability of the subject.

Embodiment 30. The method of any one of Embodiments 1-29, further comprising determining based on the electromagnetic signal reflected off the heart of the subject a respiratory rate of the subject.

Embodiment 31. The method of any one of Embodiments 1-30, further comprising determining based on the electromagnetic signal reflected off the heart of the subject a blood oxygen saturation level in the subject.

Embodiment 32. The method of any one of Embodiments 1-31, further comprising determining based on the electromagnetic signal reflected off the heart of the subject a thoracic fluid content in the subject.

Embodiment 33. A method comprising: a) receiving by a computer system data associated with an electromagnetic signal reflected off a heart of a subject; b) comparing by a processor of the computer system the data associated with the electromagnetic signal reflected off the heart of the subject to a reference; c) determining based on the comparison of the data associated with the electromagnetic signal reflected off the heart of the subject to the reference a change in pulmonary artery pressure in the subject; and d) outputting a result of the determination.

Embodiment 34. The method of Embodiment 33, wherein the determination of the pulmonary artery pressure change in the subject is determined by an analysis of a movement of a portion of the heart.

Embodiment 35. The method of Embodiment 33, wherein the determination of the pulmonary artery pressure change in the subject is determined by an analysis of a movement of a chamber of the heart.

Embodiment 36. The method of Embodiment 34 or 35, wherein the movement is an expansion of a chamber of the heart.

Embodiment 37. The method of Embodiment 34 or 35, wherein the movement is a contraction of a chamber of the heart.

Embodiment 38. The method of Embodiment 33, wherein the determination of the change in pulmonary artery pressure in the subject is determined by an analysis of a volume change of a chamber of the heart.

Embodiment 39. The method of any one of Embodiments 35-38, wherein the chamber of the heart is a right ventricle.

Embodiment 40. The method of any one of Embodiments 35-38, wherein the chamber of the heart is a left ventricle.

Embodiment 41. The method of any one of Embodiments 35-38, wherein the chamber of the heart is a right atrium.

Embodiment 42. The method of any one of Embodiments 35-38, wherein the chamber of the heart is a left atrium.

Embodiment 43. The method of any one of Embodiments 33-42, wherein the determined change in pulmonary artery pressure in the subject is associated with congestive heart failure.

Embodiment 44. The method of any one of Embodiments 33-43, wherein the wavelength of electromagnetic radiation transmitted to the heart of the subject is a radio wave.

Embodiment 45. The method of any one of Embodiments 33-44, wherein the detecting by the receiver is using continuous wave Doppler radar sensing.

Embodiment 46. The method of any one of Embodiments 33-45, wherein the detecting by the receiver is using microwave Doppler radar sensing.

Embodiment 47. The method of any one of Embodiments 33-46, wherein the Doppler radar sensing has a frequency range of about 800 MHz to about 3 GHz.

Embodiment 48. The method of any one of Embodiments 33-47, wherein the electromagnetic signal reflected off the heart of the subject has a wavelength that is below 3 GHz.

Embodiment 49. The method of any one of Embodiments 33-48, wherein the receiver is a quadrature radar receiver.

Embodiment 50. The method of any one of Embodiments 33-49, wherein the electromagnetic signal is reflected off a surface of the heart of the subject.

Embodiment 51. The method of any one of Embodiments 33-50, wherein the transceiver device, transmitting antenna, and the receiving antenna are in a common housing.

Embodiment 52. The method of any one of Embodiments 33-51, wherein the transceiver device further comprises a microcontroller, a power module, a battery, or any combination thereof.

Embodiment 53. The method of any one of Embodiments 33-52, further comprising placing the transmitter-containing device to a chest of the subject.

Embodiment 54. The method of any one of Embodiments 33-53, further comprising placing the transmitter-containing device to a sternum of the subject.

Embodiment 55. The method of any one of Embodiments 33-54, wherein the subject is human.

Embodiment 56. The method of any one of Embodiments 33-55, wherein the subject is undergoing an intervention for heart failure, the method further comprising determining based on the electromagnetic signal reflected off the heart of the subject whether the intervention for the heart failure has modulated the pulmonary artery pressure.

Embodiment 57. The method of any one of Embodiments 33-56, further comprising determining based on the electromagnetic signal reflected off the heart of the subject a cardiac output of the heart of the subject.

Embodiment 58. The method of any one of Embodiments 33-57, further comprising determining based on the electromagnetic signal reflected off the heart of the subject a cardiac rhythm of the heart of the subject.

Embodiment 59. The method of any one of Embodiments 33-58, further comprising determining based on the electromagnetic signal reflected off the heart of the subject a stroke volume of the heart of the subject.

Embodiment 60. The method of any one of Embodiments 33-59, further comprising determining based on the electromagnetic signal reflected off the heart of the subject an ejection fraction of the heart of the subject.

Embodiment 61. The method of any one of Embodiments 33-60, further comprising determining based on the electromagnetic signal reflected off the heart of the subject a heart rate variability of the subject.

Embodiment 62. The method of any one of Embodiments 33-61, further comprising determining based on the electromagnetic signal reflected off the heart of the subject a respiratory rate of the subject.

Embodiment 63. The method of any one of Embodiments 33-62, further comprising determining based on the electromagnetic signal reflected off the heart of the subject a blood oxygen saturation level in the subject.

Embodiment 64. The method of any one of Embodiments 33-63, further comprising determining based on the electromagnetic signal reflected off the heart of the subject a thoracic fluid content in the subject.

Embodiment 65. A method of detecting a heart failure condition in a subject, comprising: a) transmitting by a transmitter a wave of energy to a heart of the subject; b) detecting by a receiver a signal reflected off the heart of the subject in response to the wave of energy transmitted to the heart of the subject, wherein the signal reflected off the heart of the subject corresponds to a motion of the heart; and c) determining based on the signal reflected off the heart of the subject whether the subject has the heart failure condition.

Embodiment 66. The method of Embodiment 65, wherein the transmitting of the wave of energy is to a surface of the heart of the subject.

Embodiment 67. The method of Embodiment 65 or 66, wherein the signal reflected off the heart of the subject is reflected off a surface of a chamber of the heart of the subject.

Embodiment 68. The method of any one of Embodiments 65-67, wherein the detecting of the signal reflected off the heart of the subject is by quadrature Doppler radar.

Embodiment 69. The method of any one of Embodiments 65-68, further comprising determining based on the signal reflected off the heart of the subject an average magnitude of the motion of the heart over a time period of detection.

Embodiment 70. The method of Embodiment 69, wherein the average magnitude of the motion of the heart decreases between two time periods of detection.

Embodiment 71. The method of Embodiment 69, wherein the average magnitude of the motion of the heart increases between two time periods of detection.

Embodiment 72. The method of any one of Embodiments 69-71, wherein the time period of detection is about 1 second to about 20 seconds.

Embodiment 73. The method of any one of Embodiments 69-71, wherein the time period of detection is about 10 seconds.

Embodiment 74. The method of any one of Embodiments 69-73, wherein the time period of detection is a single heartbeat of the subject.

Embodiment 75. The method of any one of Embodiments 1-74, wherein the wave of energy is a wave of electromagnetic radiation.

Embodiment 76. The method of any one of Embodiments 1-74, wherein the wave of energy is a radio wave.

Embodiment 77. The method of any one of Embodiments 1-74, wherein the wave of energy is a microwave.

Embodiment 78. The method of any one of Embodiments 1-74, wherein the wave of energy is an x-ray.

Embodiment 79. The method of any one of Embodiments 1-74, wherein the wave of energy has a frequency that is from 800 MHz to 3 GHz.

Embodiment 80. The method of any one of Embodiments 1-79, wherein the motion of the heart is a motion of a portion of the heart.

Embodiment 81. The method of Embodiment 80, wherein the portion of the heart is a chamber of the heart.

Embodiment 82. The method of Embodiment 81, wherein the chamber of the heart is a right ventricle.

Embodiment 83. The method of Embodiment 81, wherein the chamber of the heart is a left ventricle.

Embodiment 84. The method of Embodiment 81, wherein the chamber of the heart is a right atrium.

Embodiment 85. The method of Embodiment 81, wherein the chamber of the heart is a left atrium.

Embodiment 86. The method of any one of Embodiments 1-85, further comprising positioning the transmitter in a position suitable for transmission of the wave of energy to the heart of the subject.

Embodiment 87. The method of any one of Embodiments 1-85, further comprising positioning the transmitter in contact with the subject's body.

Embodiment 88. The method of any one of Embodiments 1-85, further comprising positioning the transmitter in contact with a chest of the subject.

Embodiment 89. The method of any one of Embodiments 1-85, further comprising positioning the transmitter in contact with the subject near a sternum of the subject.

Embodiment 90. The method of any one of Embodiments 1-89, further comprising fitting the transmitter to the subject in proximity to a chest of the subject.

Embodiment 91. The method of any one of Embodiments 1-89, further comprising fitting the transmitter to the subject in proximity to a sternum of the subject.

Embodiment 92. The method of any one of Embodiments 1-91, wherein the transmitter and the receiver are in a common housing.

Embodiment 93. The method of any one of Embodiments 1-92, wherein the determining based on the signal reflected off the heart of the subject whether the subject has the heart failure condition is by a processor.

Embodiment 94. The method of any one of Embodiments 1-93, wherein the transmitter, the receiver, and the processor are in a common housing.

Embodiment 95. The method of any one of Embodiments 1-94, wherein the subject undergoes an intervention, the method further comprising determining whether the intervention causes a clinically-significant change in pulmonary artery pressure in the subject.

Embodiment 96. The method of Embodiment 95, wherein the intervention is a surgery.

Embodiment 97. The method of Embodiment 95, wherein the intervention is a heart transplantation.

Embodiment 98. The method of Embodiment 95, wherein the intervention is a beta-blocker therapy.

Embodiment 99. The method of Embodiment 95, wherein the intervention is a vasodilator therapy.

Embodiment 100. The method of Embodiment 95, wherein the intervention is an angiotensin-converting enzyme (ACE) inhibitor therapy.

Embodiment 101. The method of Embodiment 95, wherein the intervention is an angiotensin receptor blocker (ARB) therapy.

Embodiment 102. The method of Embodiment 95, wherein the intervention is a diuretic therapy.

Embodiment 103. The method of Embodiment 95, wherein the intervention is an aldosterone antagonist therapy.

Embodiment 104. The method of Embodiment 95, wherein the intervention is an inotropic agent therapy.

Embodiment 105. The method of Embodiment 95, wherein the intervention is a calcium channel blocker therapy.

Embodiment 106. The method of Embodiment 95, wherein the intervention is digoxin therapy.

Embodiment 107. The method of Embodiment 95, wherein the intervention is hydralazine and nitrates therapy.

Embodiment 108. The method of any one of Embodiments 1-107, wherein the heart failure condition is decompensated heart failure.

Embodiment 109. The method of any one of Embodiments 1-107, wherein the heart failure condition is acute decompensated heart failure.

Embodiment 110. The method of any one of Embodiments 1-107, wherein the heart failure condition is congestive heart failure.

Embodiment 111. The method of any one of Embodiments 1-107, wherein the heart failure condition is fluid accumulation in the heart.

Embodiment 112. The method of any one of Embodiments 1-107, wherein the heart failure condition is right-sided heart failure.

Embodiment 113. The method of any one of Embodiments 1-107, wherein the heart failure condition is left-sided heart failure.

Embodiment 114. The method of any one of Embodiments 1-107, wherein the heart failure condition is systolic heart failure.

Embodiment 115. The method of any one of Embodiments 1-107, wherein the heart failure condition is diastolic heart failure.

Embodiment 116. The method of any one of Embodiments 1-107, wherein the heart failure condition is Stage A heart failure.

Embodiment 117. The method of any one of Embodiments 1-107, wherein the heart failure condition is Stage B heart failure.

Embodiment 118. The method of any one of Embodiments 1-107, wherein the heart failure condition is Stage C heart failure.

Embodiment 119. The method of any one of Embodiments 1-107, wherein the heart failure condition is Stage D heart failure.

Embodiment 120. The method of any one of Embodiments 1-119, wherein the subject is human.

Embodiment 121. A method of determining a clinically-significant change in pulmonary artery pressure in a subject, comprising: a) transmitting by a transmitter a wave of energy to a heart of the subject; b) detecting by a receiver a signal reflected off the heart of the subject in response to the wave of energy transmitted to the heart of the subject, wherein the signal reflected off the heart of the subject corresponds to a motion of the heart; and c) determining based on the signal reflected off the heart of subject the clinically-significant change in pulmonary artery pressure.

Embodiment 122. The method of Embodiment 121, wherein the clinically-significant change in pulmonary artery pressure of the subject is an increase.

Embodiment 123. The method of Embodiment 121, wherein the clinically-significant change in pulmonary artery pressure of the subject is a decrease.

Embodiment 124. The method of any one of Embodiments 121-123, wherein the transmitting of the wave of energy is to a surface of the heart of the subject.

Embodiment 125. The method of any one of Embodiments 121-124, wherein the signal reflected off the heart of the subject is reflected off a surface of the heart of the subject.

Embodiment 126. The method of any one of Embodiments 121-125, wherein the detecting of the signal reflected off the heart of the subject is by quadrature Doppler radar.

Embodiment 127. The method of any one of Embodiments 121-126, further comprising determining based on the signal reflected off the heart of the subject an average magnitude of the motion of the heart over a time period of detection.

Embodiment 128. The method of Embodiment 127, wherein a change in the average magnitude of the motion of the heart is between two time periods of detection indicates that the subject has the heart failure condition.

Embodiment 129. The method of Embodiment 127, wherein the average magnitude of the motion of the heart decreases between two time periods of detection.

Embodiment 130. The method of Embodiment 127, wherein the average magnitude of the motion of the heart increases between two time periods of detection.

Embodiment 131. The method of any one of Embodiments 127-130, wherein the time period of detection is about 1 second to about 20 seconds.

Embodiment 132. The method of any one of Embodiments 127-130, wherein the time period of detection is about 10 seconds.

Embodiment 133. The method of any one of Embodiments 127-130, wherein the time period of detection is a single heartbeat of the subject.

Embodiment 134. The method of any one of Embodiments 121-133, wherein the wave of energy is a wave of electromagnetic radiation.

Embodiment 135. The method of any one of Embodiments 121-133, wherein the wave of energy is a radio wave.

Embodiment 136. The method of any one of Embodiments 121-133, wherein the wave of energy is a microwave.

Embodiment 137. The method of any one of Embodiments 121-133, wherein the wave of energy is an x-ray.

Embodiment 138. The method of any one of Embodiments 121-133, wherein the wave of energy has a frequency that is from 800 MHz to 3 GHz.

Embodiment 139. The method of any one of Embodiments 121-138, wherein the motion of the heart is a change in a portion of the heart.

Embodiment 140. The method of Embodiment 139, wherein the portion of the heart is a chamber of the heart.

Embodiment 141. The method of Embodiment 140, wherein the chamber of the heart is a right ventricle.

Embodiment 142. The method of Embodiment 140, wherein the chamber of the heart is a left ventricle.

Embodiment 143. The method of Embodiment 140, wherein the chamber of the heart is a right atrium.

Embodiment 144. The method of Embodiment 140, wherein the chamber of the heart is a left atrium.

Embodiment 145. The method of any one of Embodiments 121-144, further comprising positioning the transmitter in a position suitable for transmission of the wave of energy to the heart of the subject.

Embodiment 146. The method of any one of Embodiments 121-145, further comprising positioning the transmitter in contact with the subject's body.

Embodiment 147. The method of any one of Embodiments 121-145, further comprising positioning the transmitter in contact with a chest of the subject.

Embodiment 148. The method of any one of Embodiments 121-145, further comprising positioning the transmitter in contact with a sternum of the subject.

Embodiment 149. The method of any one of Embodiments 121-148, further comprising fitting the transmitter to the subject in proximity to a chest of the subject.

Embodiment 150. The method of any one of Embodiments 121-148, further comprising fitting the transmitter to the subject in proximity to a sternum of the subject.

Embodiment 151. The method of any one of Embodiments 121-150, wherein the transmitter and the receiver are in a common housing.

Embodiment 152. The method of any one of Embodiments 121-151, wherein the determining based on the signal reflected off the heart of the subject whether the subject has the heart failure condition is by a processor.

Embodiment 153. The method of any one of Embodiments 121-152, wherein the transmitter, the receiver, and the processor are in a common housing.

Embodiment 154. The method of any one of Embodiments 121-153, wherein the subject undergoes an intervention, the method further comprising determining whether the intervention causes a clinically-significant change in pulmonary artery pressure in the subject.

Embodiment 155. The method of Embodiment 154, wherein the intervention is a surgery.

Embodiment 156. The method of Embodiment 154, wherein the intervention is a heart transplantation.

Embodiment 157. The method of Embodiment 154, wherein the intervention is a beta-blocker therapy.

Embodiment 158. The method of Embodiment 154, wherein the intervention is a vasodilator therapy.

Embodiment 159. The method of Embodiment 154, wherein the intervention is an angiotensin-converting enzyme (ACE) inhibitor therapy.

Embodiment 160. The method of Embodiment 154, wherein the intervention is an angiotensin receptor blocker (ARB) therapy.

Embodiment 161. The method of Embodiment 154, wherein the intervention is a diuretic therapy.

Embodiment 162. The method of Embodiment 154, wherein the intervention is an aldosterone antagonist therapy.

Embodiment 163. The method of Embodiment 154, wherein the intervention is an inotropic agent therapy.

Embodiment 164. The method of Embodiment 154, wherein the intervention is a calcium channel blocker therapy.

Embodiment 165. The method of Embodiment 154, wherein the intervention is digoxin therapy.

Embodiment 166. The method of Embodiment 154, wherein the intervention is hydralazine and nitrates therapy.

Embodiment 167. The method of any one of Embodiments 121-166, further comprising determining based on the clinically-significant change in pulmonary artery pressure of the subject, whether the subject has a heart failure condition.

Embodiment 168. The method of Embodiment 167, wherein the heart failure condition is decompensated heart failure.

Embodiment 169. The method of Embodiment 167, wherein the heart failure condition is acute decompensated heart failure.

Embodiment 170. The method of Embodiment 167, wherein the heart failure condition is congestive heart failure.

Embodiment 171. The method of Embodiment 167, wherein the heart failure condition is fluid accumulation in the heart.

Embodiment 172. The method of Embodiment 167, wherein the heart failure condition is right-sided heart failure.

Embodiment 173. The method of Embodiment 167, wherein the heart failure condition is left-sided heart failure.

Embodiment 174. The method of Embodiment 167, wherein the heart failure condition is systolic heart failure.

Embodiment 175. The method of Embodiment 167, wherein the heart failure condition is diastolic heart failure.

Embodiment 176. The method of Embodiment 167, wherein the heart failure condition is Stage A heart failure.

Embodiment 177. The method of Embodiment 167, wherein the heart failure condition is Stage B heart failure.

Embodiment 178. The method of Embodiment 167, wherein the heart failure condition is Stage C heart failure.

Embodiment 179. The method of Embodiment 167, wherein the heart failure condition is Stage D heart failure.

Embodiment 180. The method of any one of Embodiments 121-179, wherein the subject is human.

Embodiment 181. A method of detecting a heart failure condition in a subject, comprising: a) during a first time period of detection: i) transmitting by a transmitter a first wave of energy to a heart of the subject; ii) detecting by a receiver a first signal reflected off the heart of the subject in response to the first wave of energy transmitted to the heart of the subject, wherein the first signal reflected off the heart of the subject corresponds to a first motion of the heart; and iii) determining a first average magnitude of the first motion of the heart over the first time period of detection; b) during a second time period of detection: i) transmitting by the transmitter a second wave of energy to the heart of the subject; ii) detecting by the receiver a second signal reflected off the heart of the subject in response to the second wave of energy transmitted to the heart of the subject, wherein the second signal reflected off the heart of the subject corresponds to a second motion of the heart; and iii) determining a second average magnitude of the second motion of the heart over the second time period of detection; c) determining a change between the first average magnitude of the first motion of the heart over the first time period of detection and the second average magnitude of the second motion of the heart over the second time period of detection; and d) determining based on the change between the first average magnitude of the first motion of the heart over the first time period of detection and the second average magnitude of the second motion of the heart over the second time period of detection whether the subject has the heart failure condition.

Embodiment 182. The method of Embodiment 181, wherein the transmitting of the first wave of energy is to a surface of the heart of the subject.

Embodiment 183. The method of Embodiment 181 or 182, wherein the first signal reflected off the heart of the subject is reflected off a surface of the heart of the subject.

Embodiment 184. The method of any one of Embodiments 181-183, wherein the detecting of the first signal reflected off the heart of the subject is by quadrature Doppler radar.

Embodiment 185. The method of any one of Embodiments 181-184, wherein the transmitting of the second wave of energy is to a surface of the heart of the subject.

Embodiment 186. The method of any one of Embodiments 181-185, wherein the second signal reflected off the heart of the subject is reflected off a surface of the heart of the subject.

Embodiment 187. The method of any one of Embodiments 181-186, wherein the detecting of the second signal reflected off the heart of the subject is by quadrature Doppler radar.

Embodiment 188. The method of any one of Embodiments 181-187, wherein the change between the first average magnitude of the first motion of the heart over the first time period of detection and the second average magnitude of the second motion of the heart over the second time period of detection is a decrease.

Embodiment 189. The method of Embodiment 188, wherein the decrease between the first average magnitude of the first motion of the heart over the first time period of detection and the second average magnitude of the second motion of the heart over the second time period of detection indicates an increase in pulmonary artery pressure in the subject.

Embodiment 190. The method of any one of Embodiments 181-187, wherein the change between the first average magnitude of the first motion of the heart over the first time period of detection and the second average magnitude of the second motion of the heart over the second time period of detection is an increase.

Embodiment 191. The method of Embodiment 190, wherein the increase between the first average magnitude of the first motion of the heart over the first time period of detection and the second average magnitude of the second motion of the heart over the second time period of detection indicates a decrease in pulmonary artery pressure in the subject.

Embodiment 192. The method of any one of Embodiments 181-191, wherein the first wave of energy is a wave of electromagnetic radiation.

Embodiment 193. The method of any one of Embodiments 181-192, wherein the second wave of energy is a wave of electromagnetic radiation.

Embodiment 194. The method of any one of Embodiments 181-193, wherein the first time period of detection is a single heartbeat of the subject.

Embodiment 195. The method of any one of Embodiments 181-194, wherein the second time period of detection is a single heartbeat of the subject.

Embodiment 196. The method of any one of Embodiments 181-195, wherein the heart failure condition is decompensated heart failure.

Embodiment 197. The method of any one of Embodiments 181-195, wherein the heart failure condition is acute decompensated heart failure.

Embodiment 198. The method of any one of Embodiments 181-195, wherein the heart failure condition is congestive heart failure.

Embodiment 199. The method of any one of Embodiments 181-195, wherein the heart failure condition is fluid accumulation in the heart.

Embodiment 200. The method of any one of Embodiments 181-195, wherein the heart failure condition is right-sided heart failure.

Embodiment 201. The method of any one of Embodiments 181-195, wherein the heart failure condition is left-sided heart failure.

Embodiment 202. The method of any one of Embodiments 181-195, wherein the heart failure condition is systolic heart failure.

Embodiment 203. The method of any one of Embodiments 181-195, wherein the heart failure condition is diastolic heart failure.

Embodiment 204. The method of any one of Embodiments 181-195, wherein the heart failure condition is Stage A heart failure.

Embodiment 205. The method of any one of Embodiments 181-195, wherein the heart failure condition is Stage B heart failure.

Embodiment 206. The method of any one of Embodiments 181-195, wherein the heart failure condition is Stage C heart failure.

Embodiment 207. The method of any one of Embodiments 181-195, wherein the heart failure condition is Stage D heart failure.

Embodiment 208. The method of any one of Embodiments 181-207, wherein the subject is human.

Embodiment 209. A method of detecting a heart failure condition in a subject, comprising: a) obtaining a first average magnitude of the first motion of the heart over a first time period of detection; b) obtaining a second average magnitude of the second motion of the heart over a second time period of detection; c) determining a change between the first average magnitude of the first motion of the heart over the first time period of detection and the second average magnitude of the second motion of the heart over the second time period of detection; and d) determining based on the change between the first average magnitude of the first motion of the heart over the first time period of detection and the second average magnitude of the second motion of the heart over the second time period of detection whether the subject has the heart failure condition.

Embodiment 210. The method of Embodiment 209, wherein the change between the first average magnitude of the first motion of the heart over the first time period of detection and the second average magnitude of the second motion of the heart over the second time period of detection is a decrease.

Embodiment 211. The method of Embodiment 210, wherein the decrease between the first average magnitude of the first motion of the heart over the first time period of detection and the second average magnitude of the second motion of the heart over the second time period of detection indicates an increase in pulmonary artery pressure in the subject.

Embodiment 212. The method of Embodiment 209, wherein the change between the first average magnitude of the first motion of the heart over the first time period of detection and the second average magnitude of the second motion of the heart over the second time period of detection is an increase.

Embodiment 213. The method of Embodiment 212, wherein the increase between the first average magnitude of the first motion of the heart over the first time period of detection and the second average magnitude of the second motion of the heart over the second time period of detection indicates a decrease in pulmonary artery pressure in the subject.

Embodiment 214. The method of any one of Embodiments 209-213, wherein the first time period of detection is a single heartbeat of the subject.

Embodiment 215. The method of any one of Embodiments 209-214, wherein the second time period of detection is a single heartbeat of the subject.

Embodiment 216. The method of any one of Embodiments 209-215, wherein the heart failure condition is decompensated heart failure.

Embodiment 217. The method of any one of Embodiments 209-215, wherein the heart failure condition is acute decompensated heart failure.

Embodiment 218. The method of any one of Embodiments 209-215, wherein the heart failure condition is congestive heart failure.

Embodiment 219. The method of any one of Embodiments 209-215, wherein the heart failure condition is fluid accumulation in the heart.

Embodiment 220. The method of any one of Embodiments 209-215, wherein the heart failure condition is right-sided heart failure.

Embodiment 221. The method of any one of Embodiments 209-215, wherein the heart failure condition is left-sided heart failure.

Embodiment 222. The method of any one of Embodiments 209-215, wherein the heart failure condition is systolic heart failure.

Embodiment 223. The method of any one of Embodiments 209-215, wherein the heart failure condition is diastolic heart failure.

Embodiment 224. The method of any one of Embodiments 209-215, wherein the heart failure condition is Stage A heart failure.

Embodiment 225. The method of any one of Embodiments 209-215, wherein the heart failure condition is Stage B heart failure.

Embodiment 226. The method of any one of Embodiments 209-215, wherein the heart failure condition is Stage C heart failure.

Embodiment 227. The method of any one of Embodiments 209-215, wherein the heart failure condition is Stage D heart failure.

Embodiment 228. The method of any one of Embodiments 209-227, wherein the subject is human.

What is claimed is:

1. A method of detecting a heart failure condition in a heart in a body of a subject, comprising:
    a) obtaining a first average motion depth of a right ventricle of the heart over a first time period of detection, wherein the first average motion depth is based on an analysis of a first electromagnetic signal that enters the body of the subject from outside the body, is reflected off the right ventricle of the heart, exits the body, and is then detected outside the body;
    b) obtaining a second average motion depth of the right ventricle of the heart over a second time period of detection, wherein the second average motion depth is based on an analysis of a second electromagnetic signal that enters the body of the subject from outside the body, is reflected off the right ventricle of the heart, exits the body, and is then detected outside the body;
    c) determining a change between the first average motion depth of the first motion average depth of the right ventricle of the heart over the first time period of detection and the second average motion depth of the second average motion depth of the right ventricle of the heart over the second time period of detection; and
    d) determining, based on the change between the first average motion depth of the first motion average depth of the right ventricle of the heart over the first time period of detection and the second average motion depth of the second motion average depth of the right ventricle of the heart over the second time period of detection, whether the subject has the heart failure condition,
    wherein the heart failure condition comprises decompensated heart failure,
    wherein the first electromagnetic signal and the second electromagnetic signal are radio waves.

2. The method of claim 1, wherein the first time period of detection is a single heartbeat of the subject.

3. The method of claim 1, wherein the second time period of detection is a single heartbeat of the subject.

4. The method of claim 1, wherein the heart failure condition further comprises acute decompensated heart failure.

5. The method of claim 1, wherein the heart failure condition further comprises congestive heart failure.

6. The method of claim 1, wherein the heart failure condition further comprises fluid accumulation in the heart.

7. The method of claim 1, wherein the heart failure condition further comprises right-sided heart failure.

8. The method of claim 1, wherein the heart failure condition further comprises left-sided heart failure.

9. The method of claim 1, wherein the heart failure condition further comprises systolic heart failure.

10. The method of claim 1, wherein the heart failure condition further comprises diastolic heart failure.

11. The method of claim 1, wherein the heart failure condition further comprises Stage A heart failure.

12. The method of claim 1, wherein the heart failure condition further comprises Stage B heart failure.

13. The method of claim 1, wherein the heart failure condition further comprises Stage C heart failure.

14. The method of claim 1, wherein the heart failure condition further comprises Stage D heart failure.

15. The method of claim 1, wherein the subject is human.

16. The method of claim 1, wherein the first average magnitude of the first average motion depth of the right ventricle is a first average amplitude of contraction of the right ventricle, wherein the second average motion depth of the right ventricle is a second average amplitude of contraction of the right ventricle.

17. The method of claim 1, wherein the first average magnitude of the first average motion depth of the right ventricle is a first average amplitude of expansion of the right ventricle, wherein the second average motion depth of the right ventricle is a second average amplitude of expansion of the right ventricle.

18. The method of claim 1, wherein the change between the first average motion depth of the right ventricle of the heart over the first time period of detection and the second average motion depth of the right ventricle of the heart over the second time period of detection is associated with a pulmonary artery pressure that is associated with the heart failure condition.

19. The method of claim 1, wherein the change between the first average depth of the right ventricle of the heart over the first time period of detection and the second average motion depth of the right ventricle of the heart over the second time period of detection is a decrease.

20. The method of claim 19, wherein the decrease between the first average motion depth of the right ventricle of the heart over the first time period of detection and the second average motion depth of the right ventricle of the heart over the second time period of detection indicates an increase in the pulmonary artery pressure in the subject.

21. The method of claim 1, wherein the change between the first average magnitude of the first average motion depth of the right ventricle of the heart over the first time period of detection and the second average motion depth of the right ventricle of the heart over the second time period of detection is an increase.

22. The method of claim 21, wherein the increase between the first average motion average depth of the right ventricle of the heart over the first time period of detection and the second average motion depth of the right ventricle of the heart over the second time period of detection indicates a decrease in the pulmonary artery pressure in the subject.

* * * * *